United States Patent [19]

Spitzer et al.

[11] Patent Number: 5,317,436
[45] Date of Patent: May 31, 1994

[54] A SLIDE ASSEMBLY FOR PROJECTOR WITH ACTIVE MATRIX MOVEABLY MOUNTED TO HOUSING

[75] Inventors: Mark B. Spitzer, Sharon; Jack P. Salerno, Waban; Paul M. Zavracky, Norwood, all of Mass.

[73] Assignee: Kopin Corporation, Taunton, Mass.

[21] Appl. No.: 872,297

[22] Filed: Apr. 22, 1992

Related U.S. Application Data

[63] Continuation-in-part of Ser. No. 839,241, Feb. 20, 1992, which is a continuation-in-part of Ser. No. 636,602, Dec. 31, 1990.

[51] Int. Cl.[5] .................. G02F 1/1333; G02F 1/13; G02F 1/1335
[52] U.S. Cl. .................. 359/83; 359/36; 359/41; 353/30; 353/120
[58] Field of Search .................. 359/41, 48, 59, 45, 359/83; 353/30, 31, 103, 120, 122, DIG. 5; 358/230, 231, 60, 61; 40/448

[56] References Cited

U.S. PATENT DOCUMENTS

| | | | |
|---|---|---|---|
| 4,024,626 | 5/1977 | Leupp et al. | 257/353 |
| 4,105,313 | 8/1978 | Altman | 359/41 |
| 4,270,846 | 6/1981 | Miyarmoto | 350/336 |
| 4,368,963 | 1/1983 | Stolov | 353/31 |
| 4,429,305 | 1/1984 | Hosokawa et al. | 340/784 |
| 4,740,782 | 4/1988 | Aoki et al. | 340/719 |
| 4,755,869 | 7/1988 | Tanaka | 358/60 |
| 4,763,993 | 8/1988 | Vogeley et al. | 359/70 |
| 4,769,680 | 9/1988 | Resor, III et al. | 355/43 |
| 4,770,498 | 9/1988 | Aoki et al. | 350/334 |
| 4,782,340 | 11/1988 | Czubatyj et al. | 340/825 |
| 4,786,966 | 11/1988 | Hanson et al. | 358/108 |
| 4,818,098 | 4/1989 | Kahn et al. | 353/122 |
| 4,850,685 | 7/1989 | Kamakura et al. | 350/397 |
| 4,864,390 | 9/1989 | McKechnie et al. | 358/60 |
| 4,904,061 | 2/1990 | Aruga | 350/339 |
| 4,909,601 | 3/1990 | Yajima et al. | 350/331 |

(List continued on next page.)

FOREIGN PATENT DOCUMENTS

| | | |
|---|---|---|
| 0352636A3 | 1/1990 | European Pat. Off. |
| 0362776A2 | 11/1990 | European Pat. Off. |
| 3142664A1 | 5/1983 | Fed. Rep. of Germany |
| 3723181A1 | 1/1989 | Fed. Rep. of Germany |
| 3933862A1 | 4/1991 | Fed. Rep. of Germany |
| 62-293221 | 12/1987 | Japan |
| 63-102572 | 5/1988 | Japan |
| 63-147151 | 6/1988 | Japan |
| 1237592 | 9/1989 | Japan |
| 2191057 | 12/1987 | United Kingdom |

OTHER PUBLICATIONS

Publication of Sumiyoshi et al. (1989), "Device layer Transferred Poly-Si TFT Array for High Resolution Liquid Crystal Projector", IDEM 89-165.

*Electron Display Devices* by John Wiley & Sons, published 1990 (England) Chapter 2 only.

Presentation of Stupp, E. H., Conference, Santa Clara, CA (Dec. 11-12, 1990) Flat Information Displays.

Conference Record of the 1991 International Display Research Conference presented at San Diego, CA (Oct. 15-17, 1991).

*Primary Examiner*—William L. Sikes
*Assistant Examiner*—Kenneth Parker
*Attorney, Agent, or Firm*—Hamilton, Brook, Smith & Reynolds

[57] ABSTRACT

A slide assembly adapted for use with a projector body, having a projector body, having a light source, an optical system and a chamber in which an image forming element can be placed. The slide assembly has a housing adapted to be positioned over the slide projector body with an active matrix display slide movably mounted to housing with a storage position in the housing and an operating position outside the housing. In the operating position the display slide is positioned in a slide projector chamber for projection of an image onto an external viewing surface.

28 Claims, 36 Drawing Sheets

OTHER PUBLICATIONS

| | | | |
|---|---|---|---|
| 4,928,123 | 5/1990 | Takafuji | 353/20 |
| 4,952,031 | 8/1990 | Tsunoda et al. | 350/342 |
| 4,963,001 | 10/1990 | Miyajima | 353/60 |
| 4,978,952 | 12/1990 | Irwin | 340/795 |
| 4,995,702 | 2/1991 | Aruga | 350/331 |
| 5,019,749 | 5/1991 | Ito | 315/224 |
| 5,020,881 | 6/1991 | Matsuda et al. | 350/333 |
| 5,037,196 | 8/1991 | Takafuji et al. | 353/122 |
| 5,041,965 | 8/1991 | Chen | 353/122 |
| 5,052,783 | 10/1991 | Hamada | 359/40 |
| 5,054,910 | 10/1991 | Kozaki et al. | 353/31 |
| 5,056,895 | 10/1991 | Kahn | 359/87 |
| 5,056,912 | 10/1991 | Hamada et al. | 353/38 |
| 5,073,013 | 12/1991 | Sonehara et al. | 359/63 |
| 5,073,772 | 12/1991 | Takafuji et al. | 340/784 |
| 5,075,798 | 12/1991 | Sonehara et al. | 359/490 |
| 5,076,543 | 12/1991 | Mandai | 353/122 |
| 5,090,800 | 2/1992 | Ushiro | 353/071 |
| 5,092,664 | 3/1992 | Miyatake et al. | 359/41 |
| 5,095,304 | 3/1992 | Young | 340/766 |
| 5,098,183 | 3/1992 | Sonehara | 353/31 |
| 5,102,217 | 4/1992 | Takafuji et al. | 353/84 |
| 5,159,363 | 10/1992 | Brauning | 353/122 |
| 5,161,027 | 11/1992 | Liu | 358/231 |
| 5,161,042 | 11/1992 | Hamada | 359/41 |
| 5,239,322 | 8/1993 | Takanashi et al. | 359/40 |

⟨or⟩

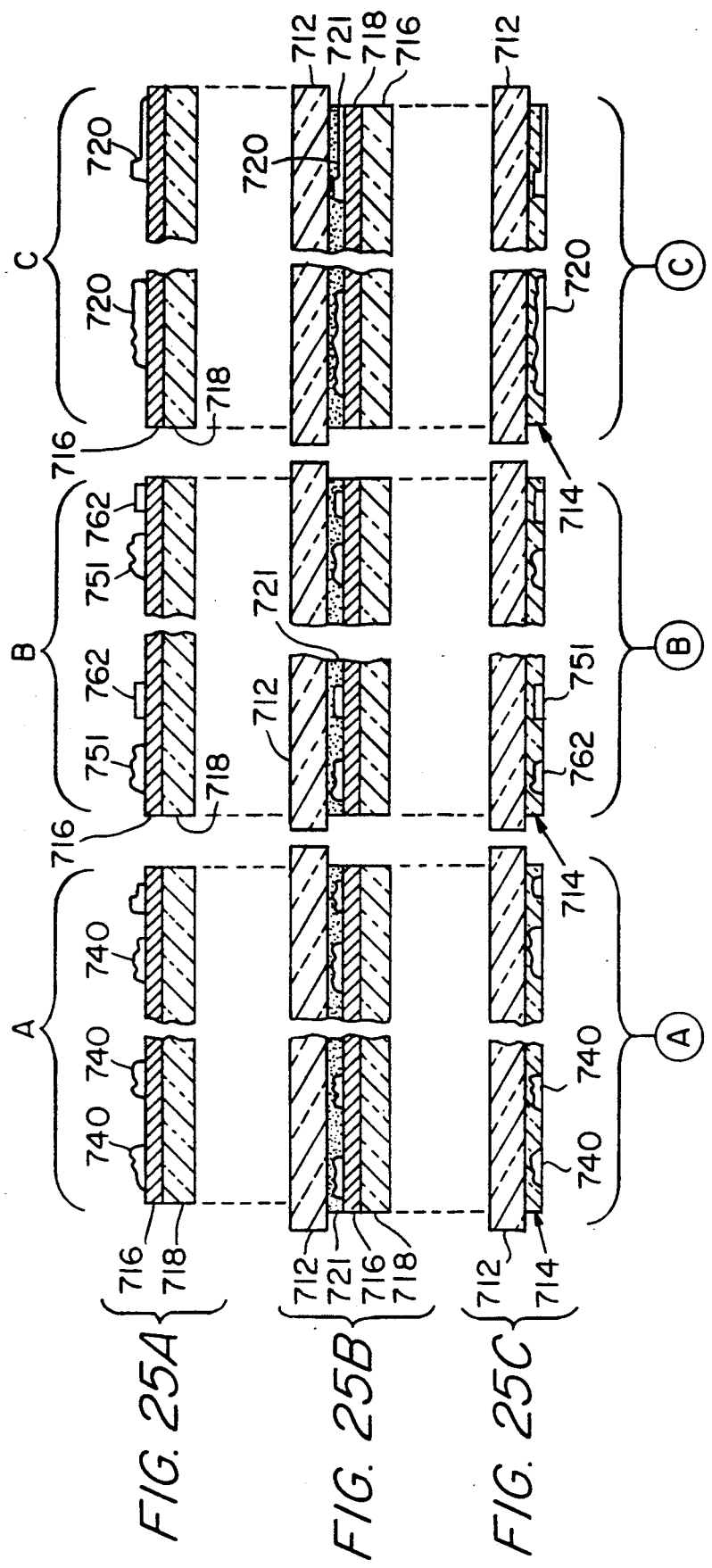

CROSS-SECTIONAL VIEW                TOP VIEW
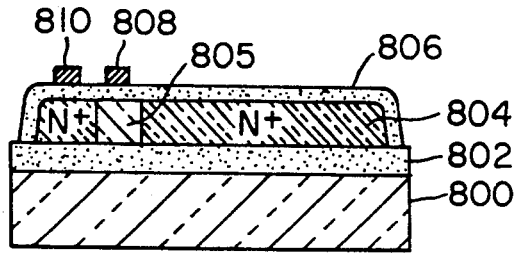 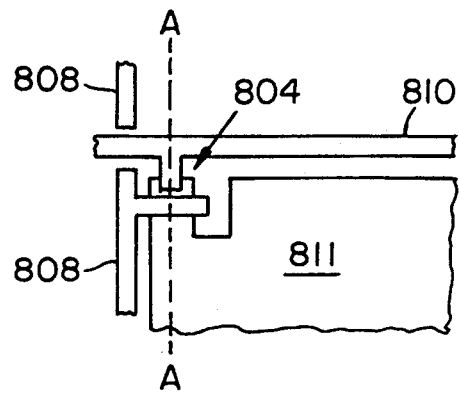
FIG. 26A
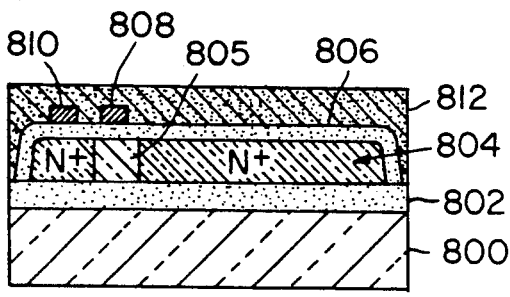 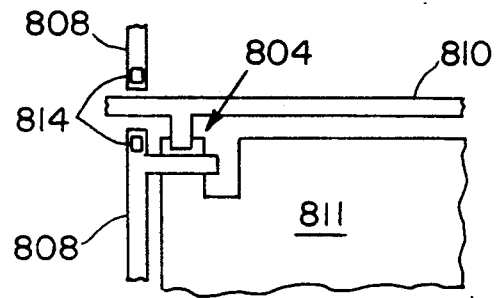
FIG. 26B
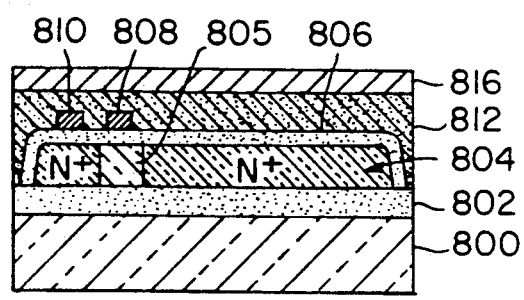 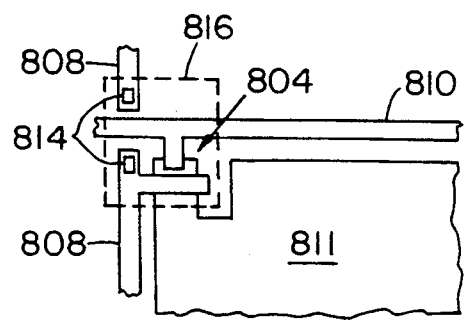
FIG. 26C

A SLIDE ASSEMBLY FOR PROJECTOR WITH ACTIVE MATRIX MOVEABLY MOUNTED TO HOUSING

RELATED APPLICATION

This document is a Continuation-In-Part of U.S. patent application, Ser. No. 07/839,241 filed Feb. 20, 1992 which is a Continuation-In-Part of U.S. patent application, Ser. No. 07/636,602 filed Dec. 31, 1990.

BACKGROUND OF THE INVENTION

Flat-panel displays are being developed which utilize liquid crystals or electroluminescent materials to produce high quality images. These displays are expected to supplant cathode ray tube (CRT) technology and provide a more highly defined television picture. The most promising route to large scale high quality liquid crystal displays (LCDs), for example, is the active-matrix approach in which thin-film transistors (TFTs) are co-located with LCD pixels. The primary advantage of the active matrix approach using TFTs is the elimination of cross-talk between pixels, and the excellent grey scale that can be attained with TFT-compatible LCDs.

Flat panel displays employing LCDs generally include five different layers: a white light source, a first polarizing filter that is mounted on one side of a circuit panel on which the TFTs are arrayed to form pixels, a filter plate containing at least three primary colors arranged into pixels, and finally a second polarizing filter. A volume between the circuit panel and the filter plate is filled with a liquid crystal material. This material will rotate the polarization of light when an electric field is applied across it between the circuit panel and a ground affixed to the filter plate. Thus, when a particular pixel of the display is turned on, the liquid crystal material rotates polarized light being transmitted through the material so that it will pass through the second polarizing filter.

The primary approach to TFT formation over the large areas required for flat panel displays has involved the use of amorphous silicon which has previously been developed for large-area photovoltaic devices. Although the TFT approach has proven to be feasible, the use of amorphous silicon compromises certain aspects of the panel performance. For example, amorphous silicon TFTs lack the frequency response needed for large area displays due to the low electron mobility inherent in amorphous material. Thus the use of amorphous silicon limits display speed, and is also unsuitable for the fast logic needed to drive the display.

Owing to the limitations of amorphous silicon, other alternative materials include polycrystalline silicon, or laser recrystallized silicon. These materials are limited as they use silicon that is already on glass which generally restricts further circuit processing to low temperatures.

Thus, a need exists for a method of forming high quality TFTs at each pixel of a panel display having the desired speed and providing for ease and reduced cost of fabrication.

SUMMARY OF THE INVENTION

The present invention relates to panel displays and methods of fabricating such displays using thin-films of essentially single crystal silicon in which transistors are fabricated to control each pixel of the display. For a preferred embodiment, the thin-film or transistor array is transferred onto an optically transmissive substrate such as glass or transparent organic films. In this embodiment, the thin-film single crystal silicon is used to form a pixel matrix array of thin-film transistors which actuate each pixel of an LCD. CMOS circuitry that is highly suitable for driving the panel display can be formed in the same thin-film material in which the transistors have been formed. The circuitry is capable of being fully interconnected to the matrix array using thin-film metallization techniques without the need for wires and wirebonding.

Each transistor, by application of an electric field or signal, serves to control the optical transmission of light from or through an adjacent material or device. For the purposes of this application the transistor and the adjacent material or device through which light from a source is transmitted is referred to as a light valve. Thus, each pixel of the panel display can be an independently controlled light valve. Examples of such light valves include LCDs or any liquid or solid state material whose light transmitting characteristics can be altered with an electric field or signal and which can be configured to provide a dense pixel array. The present devices and related methods of fabrication satisfy all of the requirements of large scale flat panel to produce highly defined color images. The transistors or switches can be paired with electroluminescent display elements (ELDs) or light emitting diodes (LEDs) to provide a display.

A preferred embodiment of the present invention utilizes large area semiconductor films, separates the films from the processing substrate, and mounts them on glass or other suitable optically transmissive materials. Films of single crystal silicon with thicknesses on the order of 2 microns or less, have been separated from epitaxial substrates, and the films have been mounted on glass and ceramics. Functional p-n junction devices such as field effect transistors ("FETs") are at least partially fabricated prior to separation and then transferred to glass. Various bonding procedures can be used for mounting on substrates including adhesives, electrostatic bonding, Van der Waal's forces or a eutectic alloy for bonding. Other known methods can also be utilized.

A preferred embodiment of the process comprises the steps of forming a thin essentially single crystal Si film on a release substrate, fabricating an array of pixel electrodes and thin-film enhancement mode transistors, and associated CMOS circuitry on the thin film. Each transistor is electrically connected to one of the pixel electrodes such that each pixel can be independently actuated by one of the transistors. The CMOS circuitry can be used to control pixel actuation and the resulting image or images that are displayed. Device fabrication can be initiated while the thin-film is still attached to the release substrate by formation of source, drain, channel and gate regions, and interconnection with pixel electrodes. By substantially completing device processing prior to transfer to the final panel substrate, a low temperature glass or polymer can be used. Alternatively, all or a portion of device fabrication can occur after release, or upon transfer of the processed film to the glass or plastic plate. After transfer, integration with color filters and liquid crystal materials completes the panel for an embodiment employing an LCD.

Preferred methods of thin-film formation processes employ silicon-on-insulator (SOI) technology where an essentially single crystal film is formed on an insulating substrate from which it can be released. For the purposes of the present application, the term "essentially single crystal" means a film in which a majority of crystals extend over a cross-sectional area, in the plane extending laterally through the film, of at least 0.1 cm$^2$ preferably in the range of 0.5–1.0 cm$^2$ or more. Such films can be formed using known techniques, on sapphire, SiO$_2$, Si wafers, carbon and silicon carbide substrates, for example.

SOI technology generally involves the formation of a silicon layer whose crystal lattice does not match that of the underlying substrate. A particular preferred embodiment uses Isolated Silicon Epitaxy (ISE) to produce a thin film of high quality Si on a release layer. This process can include the deposition of a non-single crystal material such as amorphous or polycrystalline silicon on the release layer which is than heated to crystallize the material to form an essentially single crystal silicon. The use of a release layer enables the film and circuit release using oxides beneath the active layer that can be etched without harm to the circuits.

In a preferred embodiment the entire substrate on which the epitaxial film has been formed is removed by an etch back procedure.

Alternatively, methods of chemical epitaxial lift-off, a process for transferring semiconductor material to glass or other substrates, can be applied to large area sheets of the desired semiconductor material. These or other release methods can be used to remove any thin-film single crystal material from a growth substrate for transfer onto substrates for circuit panel fabrication.

The present invention includes CMOS circuit and pixel electrode formation in a recrystallized silicon film that is then, secured to a second transfer substrate, removed from the starting wafer or substrate, and mounted on the glass or other suitable substrate to form the circuit panel. Alternatively, one can first form the circuits, bond the circuits to glass, and then separate the circuits from the substrate. The pixels are positioned in rows and columns having a planar geometry. The order of the fabrication steps allows the use of conventional fast CMOS (or other) logic onboard the glass, since the high temperature processing for these circuits are performed prior to transfer.

Another preferred embodiment involves the fabrication of a discrete array of transistor elements, transferring these elements onto a stretchable substrate which either contracts or expands to provide the desired spacing or registration of the discrete elements and then transferring these elements onto a final substrate that is including in the display panel.

Other preferred embodiments of the present invention relate to projection display devices (i.e. monitors and image projectors) including methods of fabricating such devices using thin films of single crystal silicon in which a light valve matrix (or matrices) is formed for controlling images produced by these devices. In accordance with the present invention, projection display devices employing high density single crystal silicon light valve matrices provide high resolution images compatible with 35 mm optics.

In one preferred embodiment, an optically transmissive substrate is positioned to receive light from a back-light source and a light valve matrix is secured to the substrate. In accordance with the present invention, the light valve matrix includes an array of transistors and an array of electrodes which are formed in the thin film of single crystal silicon. The light valve matrix also includes an adjacent light transmitting material, through which light from the back-light source is selectively transmitted. Preferred embodiments are directed to light valves employing a transmissive light transmitting material such as liquid crystal or a ferroelectric material, although other transmissive materials may be used. Each light valve includes a transistor, an electrode and a portion of the adjacent light transmitting material. Each transistor, by application of an electric field or signal, serves to control the optical transmission of light through the adjacent light transmitting material for a single light valve.

A driver circuit is electrically connected to the light valve matrix to selectively actuate the light valves. The drive circuitry may be formed in the same thin-film material in which the transistors and electrodes have been formed. The drive circuitry is capable of being fully interconnected to the matrix using thin-film metallization techniques without the need for wires and wire-bonding. An optical system is also provided for projecting light transmitted through the actuated light valves onto a large viewing surface.

The present devices and related methods for fabricating projectors satisfy the requirements of large screen television or monitor displays for producing highly defined color images. To that end, a projection display device can have multiple light valves each adapted to selectively transmit light of a single primary color. Further, a dichroic prism may be provided for combining the single color light transmitted by each light valve producing a multi-color light image which is projected onto a large viewing surface.

A preferred embodiment of the formation process for a light valve matrix employed in a projective display device comprises the steps of forming a thin single crystal silicon film which includes forming a layer of polycrystalline silicon on an insulating substrate and scanning the polycrystalline layer with a heat source to crystallize the layer to form a wafer of single crystal silicon. The process also comprises the steps of transferring the single crystal silicon film onto an optically transmissive substrate and attaching the film to the substrate with an adhesive, forming an array of transistors, an array of electrodes and drive circuitry on the silicon film and forming an adjacent layer of light transmitting material (for example a liquid crystal material) through which light from a back-light source may be transmitted. Each transistor is electrically connected to an electrode such that each light valve may be independently actuated by one transistor. The drive circuitry may be used to control pixel actuation and an optical system is provided for projecting the resulting images onto a large viewing surface.

Other preferred embodiments of the present invention relate to an active matrix slide adapted for use in a conventional 35 mm slide projector for providing monochrome or multi-color images. The slide is fabricated to have equivalent physical dimensions as a standard 35 mm photographic slide having an image which can be projected by a slide projector. In accordance with the present invention, the active matrix slide, being packaged to be size equivalent with a standard 35 mm slide, is insertible into a slide projector with modification thereof for generating the projected images. An electronics unit is connected to the slide and controls image generation by the slide. In preferred embodiments, the slide is capable of generating monochrome or multi-color images.

In one preferred embodiment of the invention, an active matrix slide assembly is adapted for use with a slide projector having a projector body, a light source, an optical system and a chamber in which a 35 mm slide can be placed for projection of its image onto an external viewing surface. The slide assembly includes a housing and an active matrix slide movably mounted to the housing. As such, the slide has a storage position and an operating position. The housing is positioned on the slide projector body such that the slide, being moved into the operating position, can be securely disposed in the projector chamber for selectively transmitting light from the light source to provide images for projection by the slide projector.

The housing preferably contains a shielded electronics assembly which is electrically connected to the slide for controlling image generation. The electronics assembly receives image data from an image generation device which may be a computer or any video device. Image data provided by the device is processed by the electronics and sent to the active matrix slide. Responsive to the received data, the slide actuates the individual active matrix light valves such that the illuminating light from the light source is selectively transmitted through the slide to form monochrome or multi-color images.

In another preferred embodiment, the active matrix slide assembly includes an active matrix slide and a remote electronics housing. The slide is dimensioned to be securely positioned in the chamber of the slide projector and is electrically connected to electronics in the remote housing by a cable.

In yet another preferred embodiment, the active matrix slide assembly includes an active matrix slide which is not physically connected to the electronics housing. Instead, the active matrix slide and the electronics in the housing communicate with each other via antenna elements such as RF antennas or infrared transmitter/detector elements.

As with aforementioned embodiments, an active matrix slide has an array of pixels or light valves which are individually actuated by a drive circuit. The drive circuit components can be positioned adjacent to the array and electrically connected to the light valves. As such, the individual light valves are actuated by the drive circuit so that illuminating light is selectively transmitted through the slide to form an image.

In preferred embodiments, the active matrix circuitry is formed in or on a layer of a semiconductor material such as silicon. It is noted that any number of fabrication techniques can be employed to provide preferred thin-films of polysilicon or single crystal silicon. In embodiments in which a thin-film of single crystal silicon is used, extremely high light valve densities can be achieved such that high resolution images are obtained. Other embodiments employ the use of a solid state material or any material whose optical transmission properties can be altered by the application of an electric field can be used to supply the light valves of the present invention.

BRIEF DESCRIPTION OF THE DRAWINGS

The above, and other features of the invention including various novel details of construction and combination of parts, will now be more particularly described with reference to the accompanying drawings and that pointed out in the claims. It will be understood that the particular panel display and the methods used in fabricating those panels which embody the invention are shown by way of illustration only and not as a limitation of the invention. The principal features of this invention can be employed in various embodiments without departing from the scope of the invention.

FIGS. 25A-25C are another preferred process and transfer sequence for fabricating a light valve matrix and transferring it to a support structure.

FIGS. 26A-26E are yet another preferred process and transfer sequence for fabricating a matrix and transferring it to glass substrate.

DETAILED DESCRIPTION OF PREFERRED EMBODIMENTS

Figure 1A:
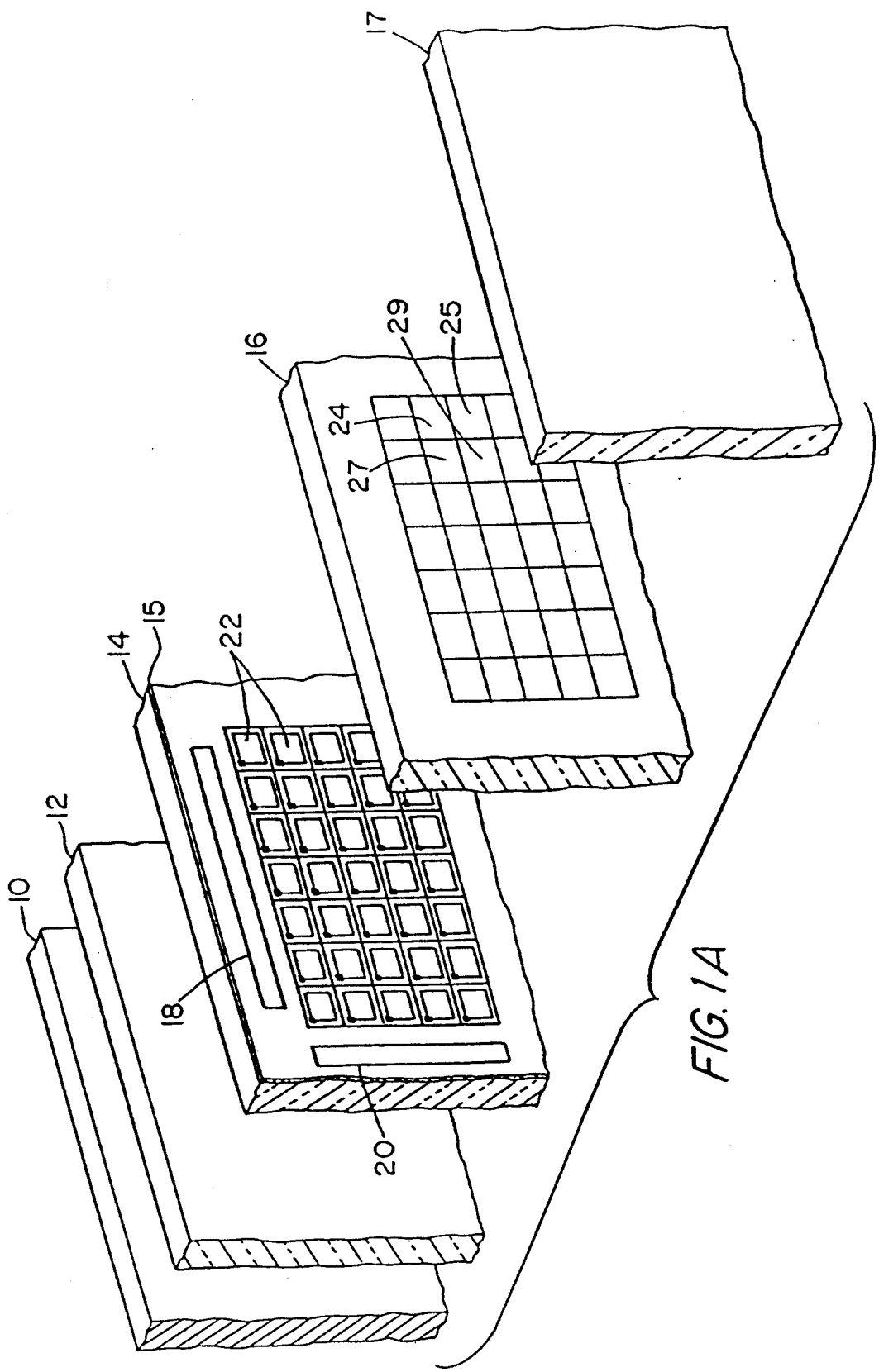
FIG. 1A is an exploded perspective view of a flat panel display in accordance with the invention.

A preferred embodiment of the invention is illustrated in the perspective view of a panel display in FIG. 1. The basic components of the display include a light source 10 that can be white or some other appropriate color, a first polarizing filter 12, a circuit panel 14, a filter plate 16 and a second polarizing filter 17, which are secured in a layered structure. A liquid crystal material (not shown) is placed in a volume between the circuit panel 14 and the filter plate 16. An array of pixels 22 on the circuit panel 14 are individually actuated by a drive circuit having first 18 and second 20 circuit components that are positioned adjacent the array such that each pixel can produce an electric field in the liquid crystal material lying between the pixel and a counter-electrode secured to the color filter plate 16. The electric field causes a rotation of the polarization of light being transmitted across the liquid crystal material that results in an adjacent color filter element being illuminated. The color filters of filter plate system 16 are arranged into groups of four filter elements such as blue 24, green 25, red 27, and white 29. The pixels or light valves associated with filter elements 24, 25, 27, 29 can be selectively actuated to provide any desired color for that pixel group.

Other preferred embodiments employ the use of a solid state material to form a light valve for each pixel. A light emitting material such as an electroluminescent film or any material whose optical transmission properties can be altered by the application of an electric field can be used to supply the light valves of the present invention.

Figure 1B:
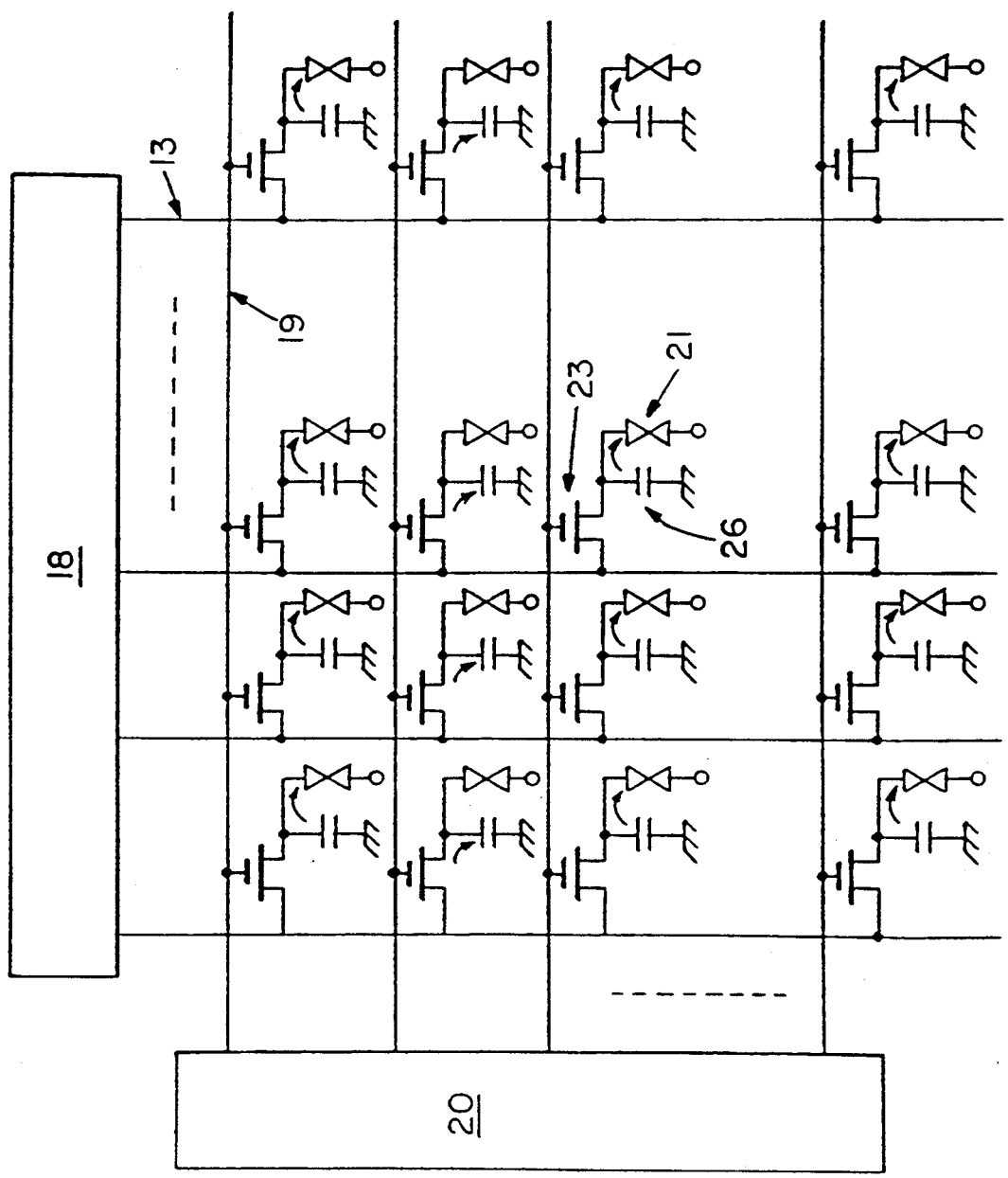
FIG. 1B is a circuit diagram illustrating the driver system for a preferred embodiment of the invention.

A drive circuit that can be used to control the display on the panel is illustrated in FIG. 1B. Circuit 18 receives an incoming signal and sends a signal to the pixels through buses 13. Circuit 20 will scan through buses 19 to turn on the individual transistors 23 which charges capacitor 26 in each pixel. The capacitor 26 sustains the charge on the pixel electrode and the liquid crystal 21 until the next scan of the array. The various embodiments of the invention may, or may not, utilize capacitors with each pixel depending upon the type of display desired.

FIGS. 2A-2L illustrate the use of an Isolated Silicon Epitaxy (ISE) process, to form silicon-on-insulator (SOI) films in which circuit panel circuitry is formed. Note that any number of techniques can be employed to provide a thin-film of single crystal Si. An SOI structure, such as that shown in FIG. 2A, includes a substrate 30 and an oxide 34 (such as, for example, $SiO_2$) that is grown or deposited on the substrate 30. A thin single crystal layer of silicon is formed over the oxide 34. The oxide (or insulator) is thus buried beneath the Si surface layer. For the case of ISE SOI structures, the top layer is a substantially single-crystal recrystallized Silicon, from which CMOS circuits can be fabricated. The use of a buried insulator provides devices having higher speeds than can be obtained in conventional bulk (Czochralski) material. Circuits containing in excess of 1.5 million CMOS transistors have been successfully fabricated in ISE material.

Figure 2A:
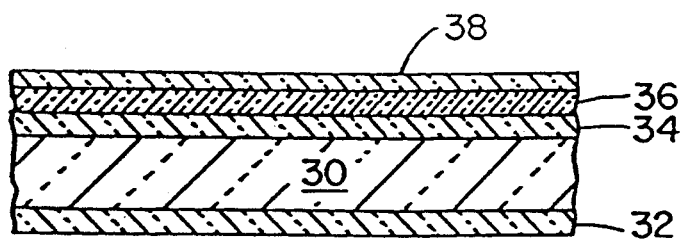
FIGS. 2A-2L is a preferred process flow sequence illustrating the fabrication of a circuit panel for a flat panel display.
Figure 2B:
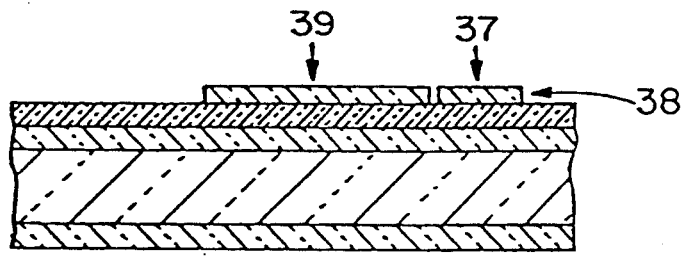
Figure 2C:
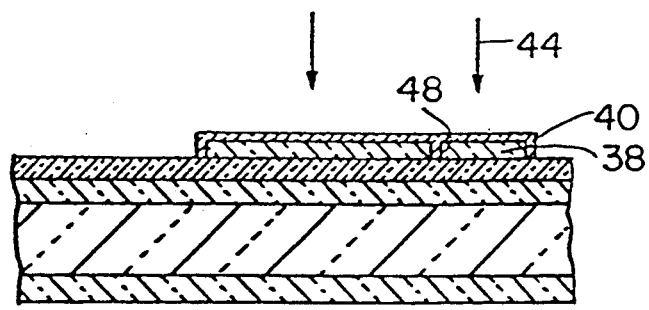

As shown in FIG. 2B, the film 38 is patterned to define a transistor region 37 and a pixel electrode region 39 for each pixel. An oxide layer 40 is then formed over the patterned regions including channel 48 between the two regions 37, 39 of each pixel. The intrinsic crystallized material 38 is than implanted 44 (at FIG. 2C) with boron or other p-type dopant to provide a n-channel device (or alternatively, an n-type dopant for an p-channel device).

Figure 2D:
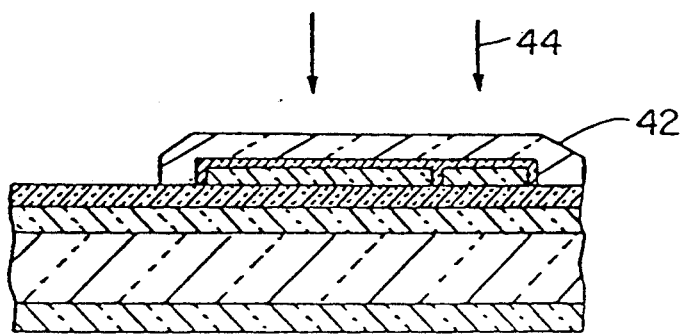
Figure 2E:
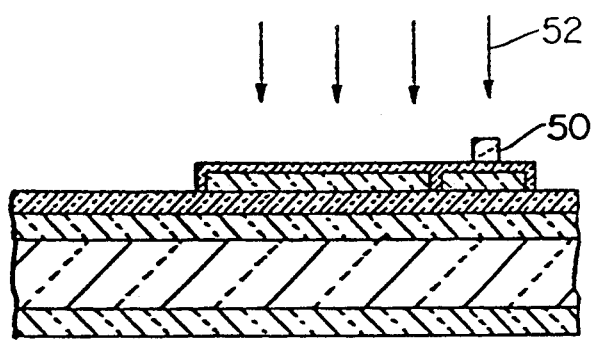
Figure 2F:
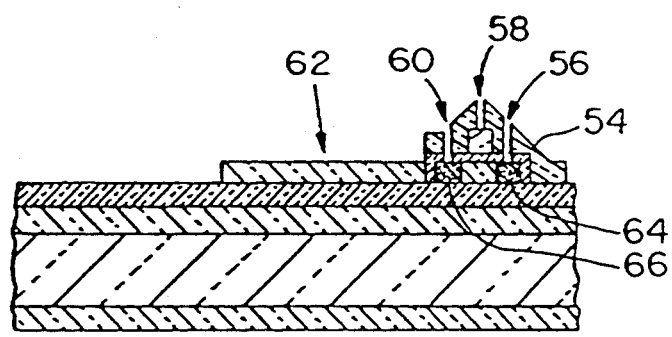
Figure 2G:
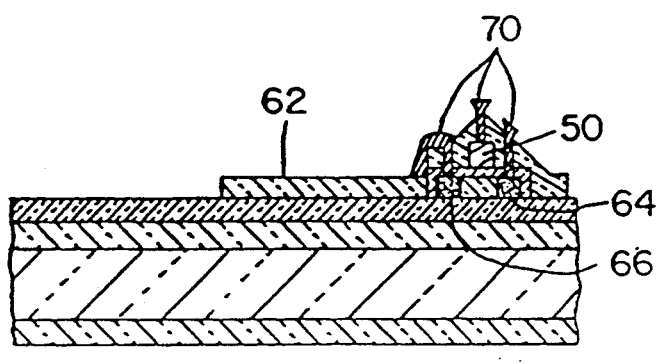
Figure 2H:
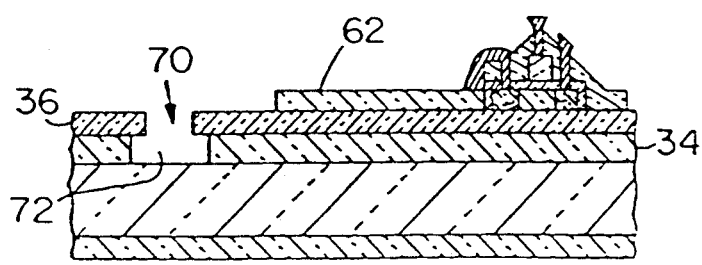

A polycrystalline silicon layer 42 is then deposited over the pixel and the layer 42 is then implanted 46, as seen in FIG. 2D, with an n-type dopant to lower the resistivity of the layer 42 to be used as a gate. The polysilicon is patterned to form the gate 50, as seen in FIG. 2E, which is followed by a large implant 52 of boron to provide p+ source and drain regions for the transistor. As shown in FIG. 2F, an oxide 54 is formed over the transistor and openings 60, 56, 58 are formed through the oxide 54 to contact the source 66, the drain 64, and the gate, respectively. A patterned metalization 70 of aluminum, tungsten or other suitable metal is used to connect the exposed pixel electrode 62 to the source 60 (or drain), and to connect the gate and drain to other circuit panel components.

A second fabrication procedure is one of the substrate release processes that have been developed to form thin (1 to 5 micron) films of processed silicon bonded to glass; these films contain active semiconductor devices such as FETs that are partially of completely fabricated prior to transfer. The crystallization and release procedures including the cleavage of laterally grown epitaxial films for transfer (CLEFT) approach are described more fully in U.S. Pat. No. 4,727,047 incorporated herein by reference. The chemical epitaxial lift-off (CEL) approach is described more fully in U.S. Pat. Nos. 4,846,931 and 4,883,561. Both of the CLEFT and CEL techniques permit the reuse of the substrate, leading to reduced cost compared to other approaches in which the substrates are consumed. By combining thin film release techniques with SOI wafers, we will be able to form the required high quality films and circuits on glass.

The foregoing indicates that CEL processes can be limited by the lateral distance that is required for the HF (or other etchant) undercut of the release layer. The key to large area panels using CEL is the release of patterned devices and/or circuits rather than complete large-area films, because the circuits or devices have unused areas that can be used as vertical channels through the film to allow the etch to reach the release layer. This approach is illustrated in FIGS. 2H–2L. To remove the circuit from the release substrate a first opening 70 (in FIG. 2H) is formed in an exposed region of layer 36 that occurs between pixels. A second larger portion of layer 34 is than removed to form cavity 72 such that a portion of layer 36 extends over the cavity 72.

Figure 2I:
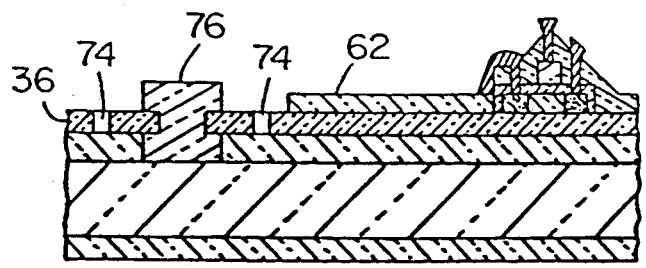
Figure 2J:
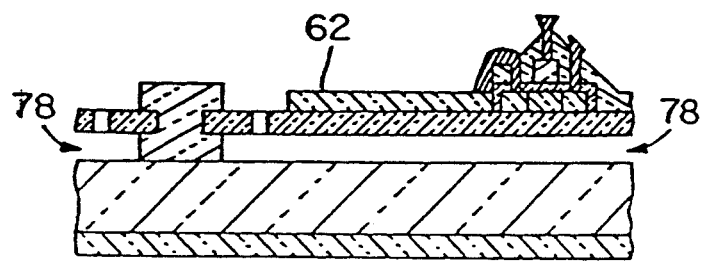
Figure 2K:
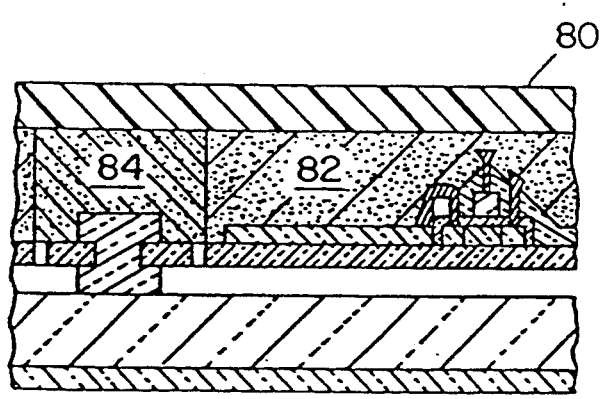

In FIG. 2I, a support post 76 is formed to fill cavity 72 and opening 70, and which extends over a portion of layer 36. Openings or via holes 74 are then provided through layer 36 such that an etchant can be introduced through holes 74, or lateral openings 78, to remove layer 34 (see FIG. 2J). The remaining insulating layer 36 and the circuitry supported thereon is now held in place relative to substrate 30 with support posts 76.

An epoxy that can be cured with ultraviolet light is used to attach an optically transmissive substrate 80 to the circuitry, and layer 36. The substrate 80 is than patterned such that regions of epoxy 84 about the posts 76 remain uncured while the remaining epoxy 82 is cured (see FIG. 2K). The substrate 30 and posts 76 are removed to provide the structure shown in FIG. 2L, which is than processed to provide the desired display panel.

Note that the UV-cured adhesive (or tape) can be patterned to protect the circuits where necessary, and HF can be used to reach the remaining the release layer.

Note that where tape is used, tape provides support to the circuits after release. Large area GaAs devices containing films have been fabricated in this way, and these have been released to form devices from entire wafers on one tape. The released circuits can be remounted on the glass and the other elements of the liquid crystal display panel. Transparent adhesives are the preferred method of mounting.

Figure 2L:
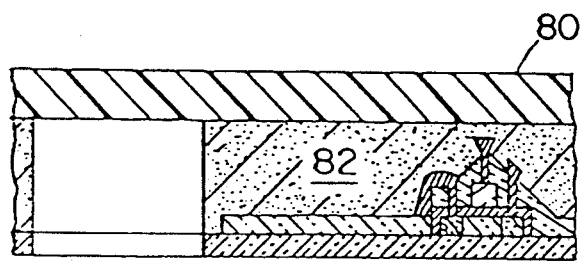

To form the final display panel the circuit panel shown in FIG. 2L is etched leaving the desired pixel elements exposed. Insulation and alignment layers, spacers, a sealing border and bonding pads for connections as added onto the circuit panel. A screen printing process can be used to prepare the border. The plate containing the color filters and the counterelectrode is sealed to the circuit panel with the sealing border after insertion of spacers. The display is filled with the selected liquid crystal material via a small filling hole or holes extending through the border. This filling hole is then sealed with a resin or epoxy. First and second polarizer films or layers are than bonded to both sides and connectors are added. Finally, a white light source 114, or other suitable light source, is coupled to polarize 112

Figure 3:
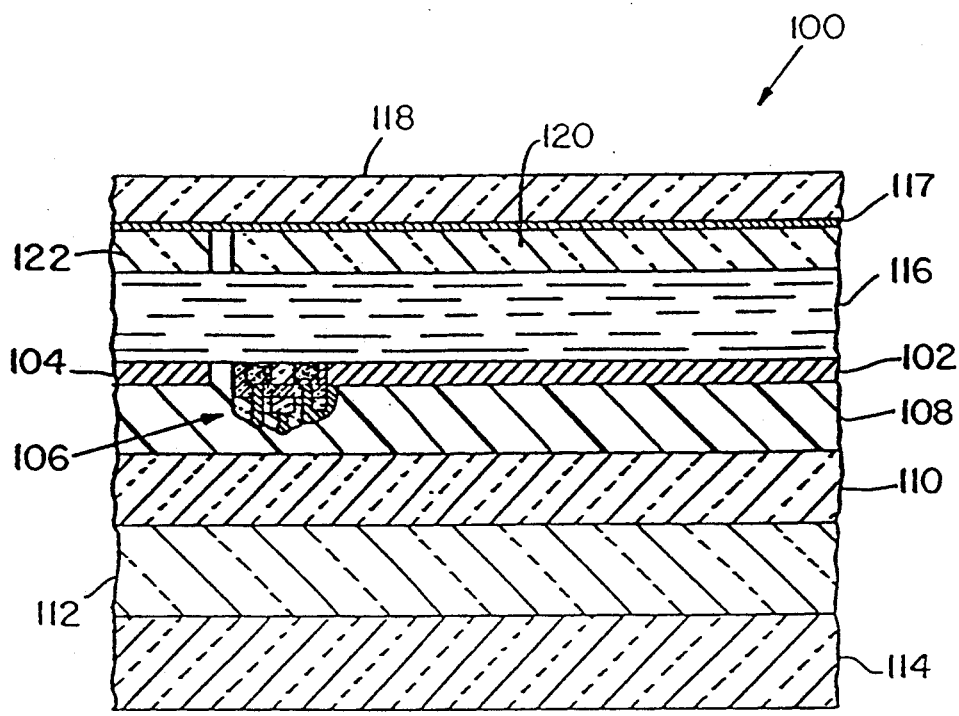
FIG. 3 is a cross-sectional view of a preferred embodiment of the display panel.

A cross-sectional view of the resulting device is shown in FIG. 3 wherein pixel electrodes 102 and 104 are laterally spaced from each other. Each pixel 102, 104 will have a transistor 106 and a color filter 120, 122 associated therewith. Polarizing elements 112, 118 are positioned on opposite sides of the structure which also includes bonding element or adhesive 108 and optically transmissive substrate 110, such as glass or plastic. Layer 108 can be a transparent epoxy or a low temperature glass that can have a thickness of 2–10 microns.

The CLEFT process permits the separation of a thin single-crystal films, grown by chemical vapor deposition (CVD), from a reusable homoepitaxial substrate. Unlike the CEL process, in the CLEFT process the circuits or devices are first bonded to glass and after mounting the separation is made between the circuits and the substrate.

The films removed from the substrate by CLEFT are essentially single-crystal, of low defect density, are only a few microns thick, and consequently the circuit panel has little weight and good transmission characteristics. For the purposes of the present application, the term "essentially single crystal" means a film in which a majority of crystals extend over a cross sectional area in a plane of the film of at least 0.1 cm$^2$, and preferably in the range of 0.5–1.0 cm$^2$ or more.

The CLEFT process, illustrated in U.S. Pat. No. 4,727,047 involves the following steps: growth of the desired thin film over a release layer (a plane of weakness), formation of metallization and other coatings, formation of a bond between the film and a second substrate such as glass (or superstrate), and separation along the built-in-plane of weakness by cleaving. The substrate is then available for reuse.

The CLEFT process is used to form sheets of essentially single crystal material using lateral epitaxial growth to form a continuous film on top of a release layer. For silicon the lateral epitaxy is accomplished by the ISE process or other recrystallization procedures. Alternatively, other standard deposition techniques can be used to form the necessary thin-film essentially single crystal material.

One of the necessary properties of the material that forms the release layer is the lack of adhesion between the layer and the semiconductor film. Since a weak plane has been created by the release layer, the film can be cleaved from the substrate without any degradation. The release layers can comprise multi-layer films of $Si_3N_4$ and $SiO_2$. Such an approach permits the $SiO_2$ to be used to passivate the back of the CMOS logic. (The $Si_3N_4$ is the layer that is dissolved to produce the plane of weakness.) In the CLEFT approach, the circuits are first bonded to the glass, or other transfer substrate, and then separated resulting in simpler handling as compared to UV-cured tape.

In the ISE process, the oxide film is strongly attached to the substrate and to the top Si film which will contain the circuits. For this reason, it is necessary to reduce the strength of the bond chemically. This technique involves a release layer that is preferentially dissolved with an etchant without complete separation, to form a plane of weakness in the release layer. The films can then be separated mechanically after the glass is bonded to the circuits and electrodes.

Mechanical separation is accomplished as follows: The upper surface of the film is bonded with a transparent epoxy to a superstrate such as glass. The film and glass are then bonded with wax to glass plates about 5 mm thick that serve as cleaving supports. A metal wedge is inserted between the two glass plates to force the surfaces apart. Since the mask has low adhesion to the substrate, the film is cleaved from the substrate but remains mounted on the glass. The substrate can then be used for another cycle of the CLEFT process, and the device processing is completed on the back surface of the film. Note that since the device remains attached to a superstrate, the back side can be subjected to standard wafer processing, including photolithography.

The method further involves the preparation of single crystal films, with seeding in the case of an Si substrate and without seeding for the case of foreign substrates. For the case of seeded Si films, the standard recrystallization process is employed. In either case, the bottom oxide or nitride layer can be optimized for release purposes.

Figure 4:
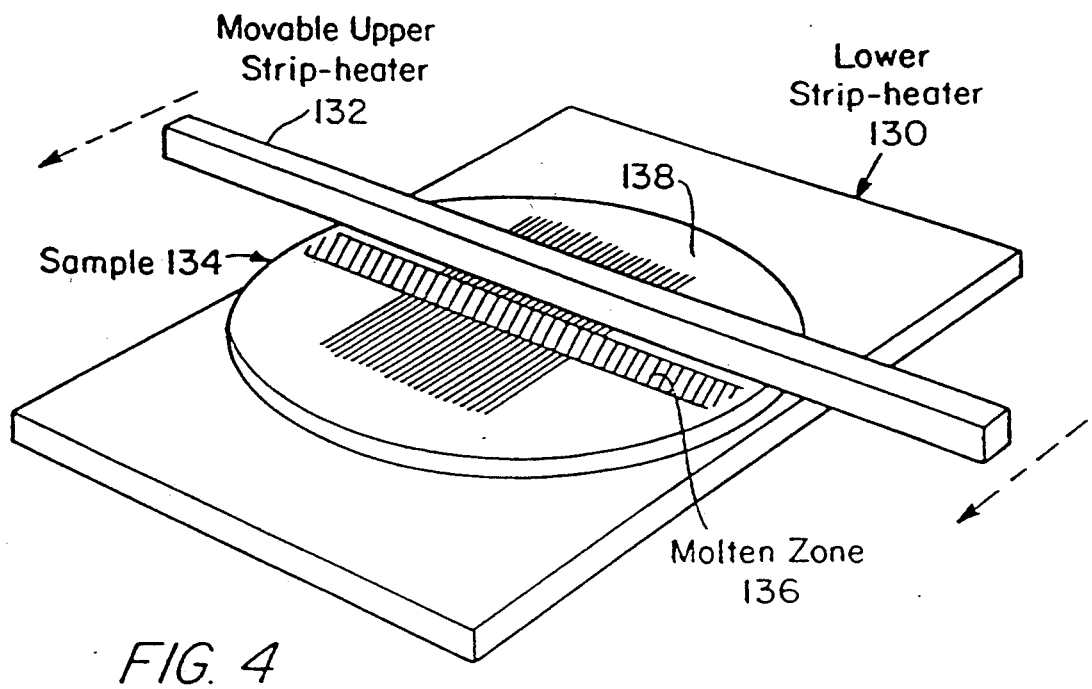
FIG. 4 illustrates in a perspective view a preferred embodiment of a system used for recrystallization.

In one embodiment of the recrystallization system, shown schematically in FIG. 4 the substrate temperature is elevated to near the melting point by a lower heater 130. An upper wire or graphite strip heater 132 is then scanned across the top of the sample 134 to cause a moving melt zone 136 to recrystallize or further crystallize the polycrystalline silicon. In the standard process on Si, the lateral epitaxy is seeded from a small opening through the lower oxide, and the resultant single crystal film has the orientation of the substrate. Capping layer 138 is deposited over the polycrystalline material prior to crystallization.

Figure 5A:
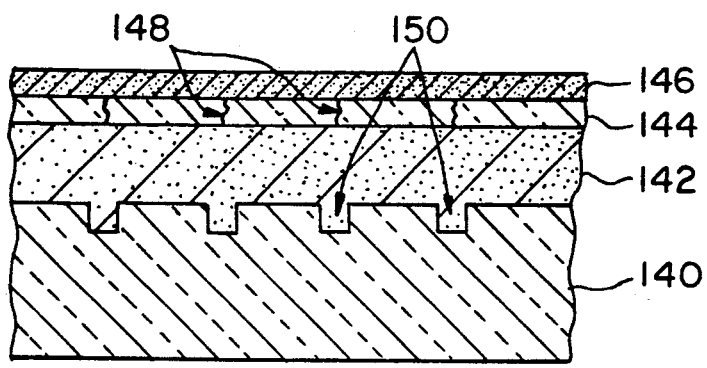
FIG. 5A illustrates the use of a patterned release layer to entrain boundaries in a crystallized material.

The use of foreign substrates precludes seeding. In this case, essentially single crystal Si is obtained by grain boundary entrainment techniques. Grain boundary entrainment can be used by patterning either the release oxide or the cap layer to introduce a modulation in the thermal gradients in the regrowth region. This modulation in the temperature field changes the location of the melt front and entrains the boundaries in predictable locations. Patterning of the release oxide 142 is shown in FIG. 5A. In this embodiment the substrate 140 has grooves 150 which are filled with the release oxide 142. Owing to this entrainment of boundaries 148 in the crystallized material 144 that can extend between the cap 146 and the release layer 142, the Si circuits or electrodes can be located in regions of high quality. Metallization and other features can be located over subgrain boundaries.

As shown, a preferable technique is to pattern the reusable substrate with the necessary entrainment structure. Once patterned in this way, the reusable substrate would not require repatterning. In such a scheme the entraining grooves are provided with a material of sufficient thickness to entirely fill the grooves. The material in the grooves could for example, comprise planarized $Si_3N_4$, while the release layer could comprise further deposition of $SiO_2$. Alternatively, the grooves could be filled entirely with $SiO_2$; the grooves could then function as channels for the release etch.

Figure 5B:
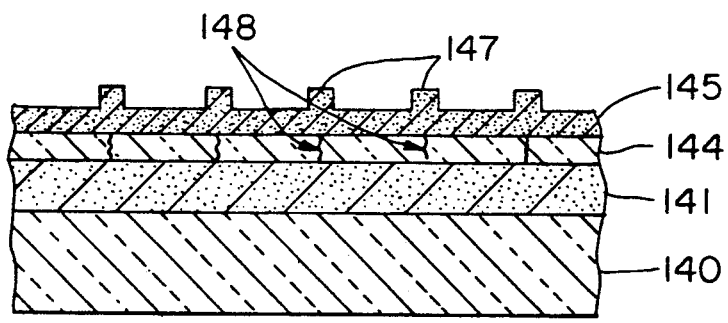
FIG. 5B illustrates the use of a patterned capping layer to entrain boundaries.

A second approach involves patterning the cap layer 145 after cap deposition, as shown in FIG. 5B. Patterned ridges 147 of the cap 145 overlie boundaries 148 in the recrystallized material that can extend between the cap 145 and release layer 141. A third approach would be to pattern the polycrystalline silicon layer.

Capping layers can be used with foreign substrates. The capping layer must be adherent throughout the thermal cycle, but must be removable for device processing. A cap works well for smooth Si substrates, but the patterned layers necessary for entrainment can require new films.

Figure 6A:
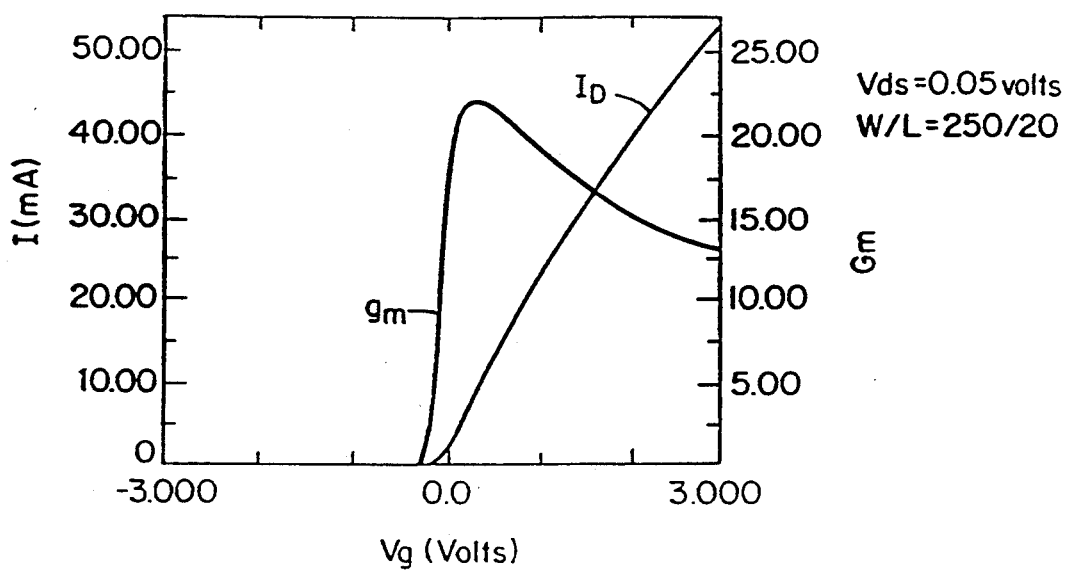
FIG. 6A illustrates the drain current and transconductance characteristics for a MOSFET prior to transfer to glass in accordance with the invention.
Figure 6B:
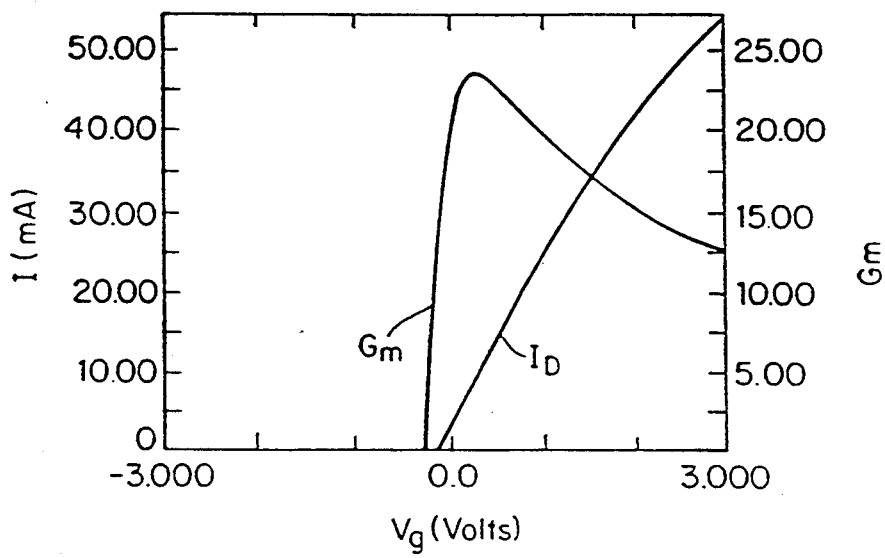
FIG. 6B illustrates the drain current and transconductance characteristics for the MOSFET of FIG. 6A after transfer to glass.

FIGS. 6–8 illustrate the electrical characteristics of a MOSFET made in accordance with the invention before and after transfer onto a glass substrate. FIG. 6A graphically depicts the drain current $I_D$ and the transconductance $G_M$ as a function of gate voltage $V_G$ in the linear region, where the drain-source voltage is 50 mV, for a MOSFET prior to transfer to glass. The MOSFET has a width-to-length ratio of 250 $\mu$m/20 $\mu$m and a gate oxide thickness of 890 A in a 0.5 $\mu$m thick recrystallized silicon material. FIG. 6B shows the drain current $I_D$ and transconductance $G_M$ of the same device after transfer to glass.

Figure 7A:
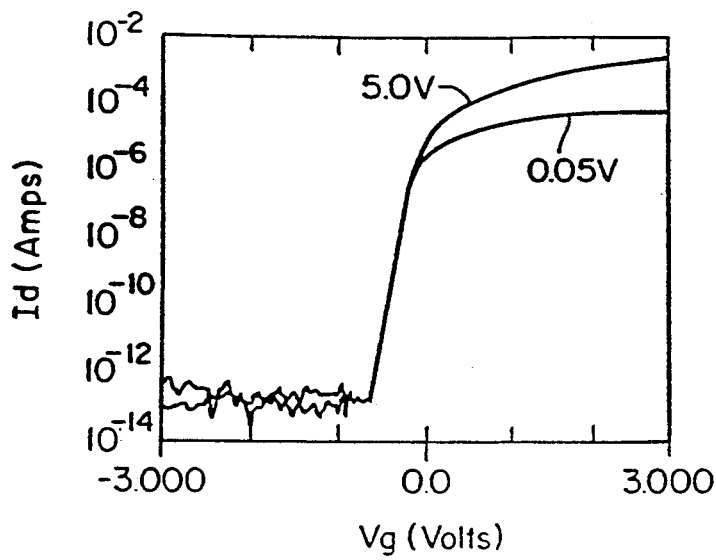
FIG. 7A illustrates the drain current of the device in FIG. 6A plotted on a logarithmic scale at two different drain voltages.

FIG. 7A graphically illustrates the drain current of the device of FIG. 6A plotted on a logarithmic scale at two drain-source voltages $V_{DS}=50$ mV and $V_{DS}=5$ V.

Figure 7B:
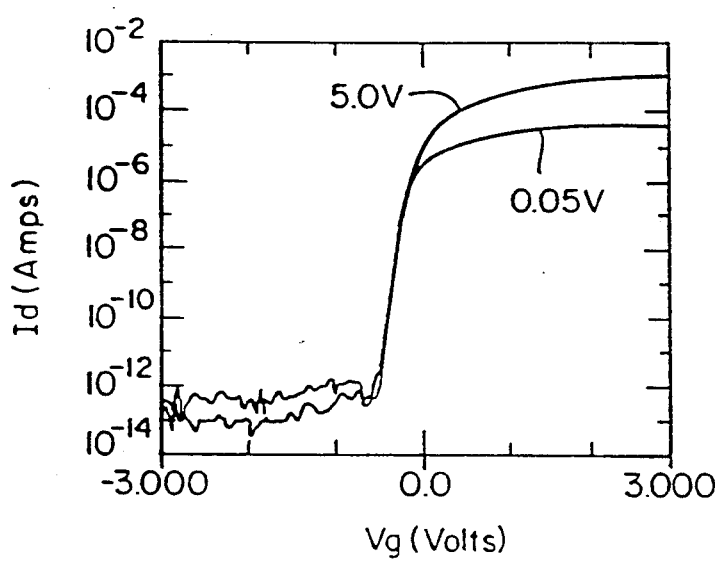
FIG. 7B illustrates the drain current of the device in FIG. 6B plotted on a logarithmic scale at two different drain voltages.

FIG. 7B graphically illustrates the drain current of the device in FIG. 6B poltted on a logarithmic scale at drain-source voltages of $V_{DS}=50$ mV and $V_{DS}=5$ V.

Figure 8A:
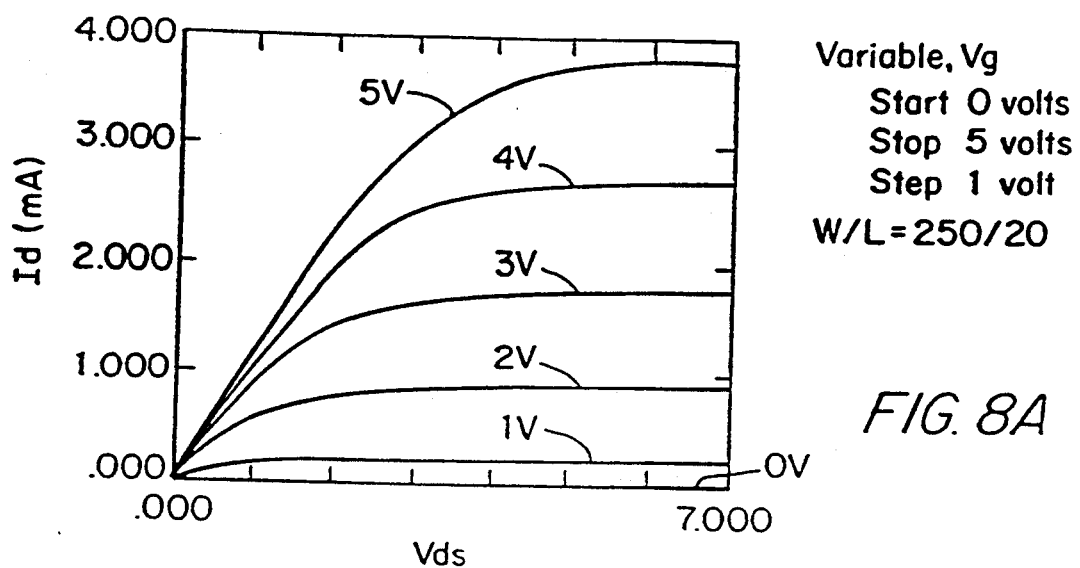
FIG. 8A illustrates the drain current output of the device of FIG. 6A with the gate voltage varying between 0 and 5 volts.

FIG. 8A graphically illustrates the drain current $I_D$ as a function of drain-source voltage of the device of FIG. 6A at gate voltages of $V_{GS}=0, 1, 2, 3, 4$ and 5 volts.

Figure 8B:
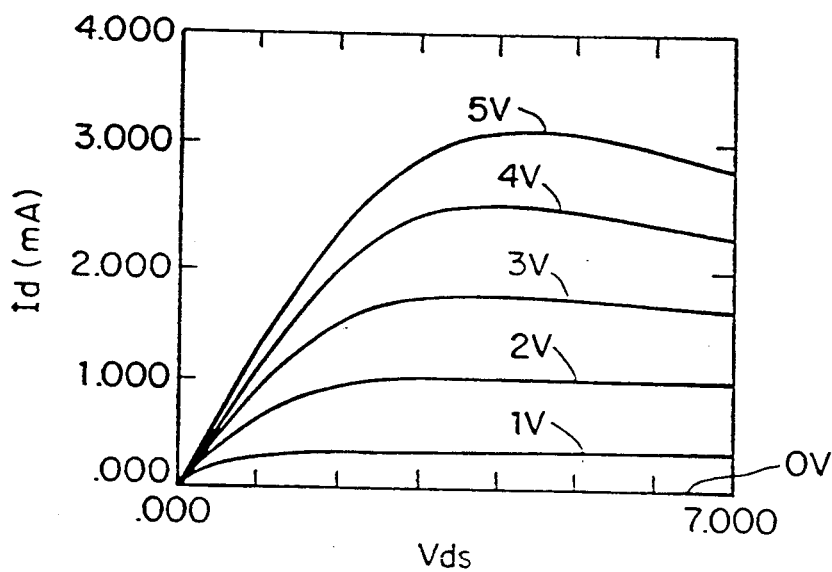
FIG. 8B illustrates the drain current output of the device of FIG. 6B with the gate voltage varying between 0 and 5 volts.

FIG. 8B graphically illustrates the drain current $I_D$ as a function of drain-source voltage of the device of FIG. 6B at gate voltages of $V_{GS}=0, 1, 2, 3, 4$ and 5 volts.

For the CEL approach, a further embodiment involves remounting of the released circuits on glass plates. The application method insures uniform intimate contact between the thin-film semiconductor and the adhesive, yet must not crack or introduce other defects in the thin films.

Methods involve the application of Apiezon W wax to the frontside of the layer to be separated. The stress in the wax imparts a curvature to the lifting layer thereby allowing the etching fluid access to the etching front. Access to the etching front is achieved only from the outer edge of the total area being lifted off.

This process is of limited use for applications involving large area liftoff, however, due to long liftoff times that can extend up to hours or days for areas larger than 2 cm $\times$ 2 cm. Curvature is required to increase etchant access to the etching front. However, the curvature necessary for liftoff is caused by a low temperature wax so that no high temperature processing can be done while this wax is present. Present samples are often cleaved to size, not allowing for substrate reuse. The wax application process is automated and patternable to allow for substrate reuse in applications where this procedure is preferred. This process is useful only for individual small areas that do not require backside processing.

Figure 9A:
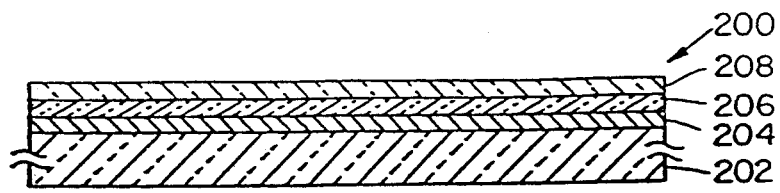
FIGS. 9A-9C are a series of cross-sectional diagrams illustrating a lift-off process in accordance with the invention.
Figure 9B:
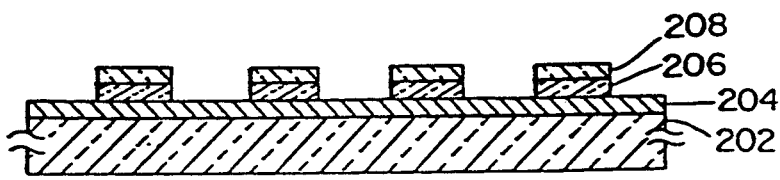
Figure 9C:
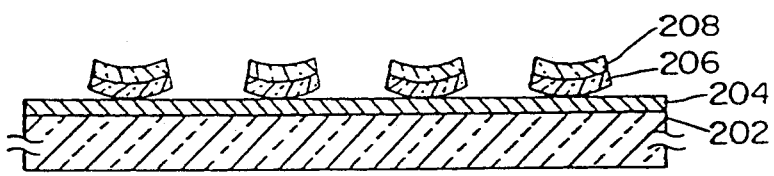

Another embodiment of the invention involves using a combination of thin or thick film materials with different coefficients of expansion to replace the black wax in the standard liftoff process. This process is illustrated in FIGS. 9A-9C. By using the correct temperature the curvature needed for liftoff is achieved due to the differential stresses in the layers. A single layer can be used if it has the correct expansion coefficient with respect to the material being lifted off. This method allows for support layers that impart the correct curvature at the liftoff temperature, lay flat at room temperature, and also support the film during backside processing.

This embodiment of the invention will now be described in connection with structure 200 of FIGS. 9A-9C. A substrate 202, which can comprise any suitable substrate material upon which epitaxial layers or devices can be formed, is provided. A release layer 204 is grown, preferably by CVD, on substrate 202. For a thin-film silicon releasable layer, an $SiO_2$ layer can be used as previously described.

A semiconductor layer structure 206 is formed on release layer 204, also by CVD or other previously described methods. Structure 206 preferably comprises materials arranged for the fabrication of an array of transistors in accordance with the invention.

By using CVD, for example, structure 206 can be made very thin, i.e., less than about 5 microns and, preferably, less than 2 microns, with the contact layer being less than 0.1 micron thick.

The necessary dopants are typically introduced by diffusion or implant after the growth processes to define source, drain and channel regions. Next, the structure 206 is processed on the front, or top side, using conventional techniques to form gates and metal contacts where each pixel is to be located and buss bars and bonding pads, as required.

In a first lift-off embodiment, a coating 208 is then formed on the front side processed structure 206 (FIG. 9A). The coating consists of a combination of thick or thin film materials with different thermal coefficients of expansion. For example, coating 208 can comprise a nitride, metal, bi-metal or a glass stressed coating. Contact metallization (not shown) can also be applied at this time on the contact layer.

The coating layer 208 and structure 206 are then patterned using conventional photolithography and the coating material 208 and structure 206 is removed in predetermined areas down to release layer 204 as shown in FIG. 9B, by etching with a suitable selective etchant. The above steps are performed at a predetermined temperature which is sufficiently low no significant thermal stress between the coating materials of coating 208 is produced. Next, the temperature is elevated to a sufficient degree, causing thermal stress in the coating 208. While at this elevated temperature the structure is exposed to a release etchant (See FIG. 9C).

The release etchant eventually etches the release layer 204 sufficiently to allow separated device structures 206 supported by the coating 208 to be removed. These structures are then brought down to a lower temperature at which the thermal stress is relieved to allow the discrete devices to lay flat for subsequent backside processing.

This process provides a significant advantage over the Gmitter et al. black wax process in that it enables the discrete chips to lay flat for backside processing and the support structure is formed of materials, such as glass, which are impervious to the backside processing temperatures.

Two different procedures can be used to achieve wafer scale liftoff. The first method involves the etching of the entire substrate on which the film to be transferred has been formed. This is termed an "etch back" procedure.

A second method accesses the release layer from the edge of the wafer or sample only and releases the material as one large sheet. This second method is for cases which do not require registration between devices lifted from the same wafer. If registration is not desired, an automated procedure is used for lift-off of large areas of individual devices or areas of material. After frontside processing is completed, UV cured epoxy can be cured with the desired pattern, removed where it is not wanted, and then used as the mask for etching down to the release layer. The UV cured epoxy can then be left on and can act as support for the lifted films after separation. The separate devices would need to be retrieved from the etching solution and processed separately using pick and place type methods.

These alternative lift-off processes will now be described in connection with FIGS. 10A-10E, wherein corresponding items in FIG. 9 retain the same reference numeral of FIG. 10. As shown in the partial perspective cross-section of FIG. 10A, a substrate 202 has formed thereon a release layer 204, followed by a device structure 206, all as described in connection with FIG. 9. All front side processing, such as bonding pads and metal contacts (not shown) to the structure 206 are completed.

A material which can be transformed from a less soluble or less etchable state to a more soluble or more etchable state (or vice versa) is formed on the front-side processed structure 206. For example, a UV curable epoxy 230 can be spread over the structure 206. This epoxy has the property that exposure to UV light causes it to be less soluble.

A UV light transparent mask release layer 232 of material is then formed over the epoxy 230 and a patterned opaque mask 234 with openings 236 is affixed over the layer 232.

The mask 234 is irradiated with UV light, curing the areas of the epoxy underlying the mask openings 236 and making them less soluble than in the uncured state. The release layer 232 is removed and the mask 234 is removed. Next, the uncured epoxy is removed by a solvent, such as down to the release layer 204 (See FIG. 10B).

The cured epoxy 230 is left on the structure to serve as a support for the thin film structure 206 after separation from the release layer 204. In this manner, the etching front is increased by dividing up the total top surface area of structure 206 into smaller areas by cutting channels 240 down to the release area 204.

A second method for wafer size lift-off relies on increasing the amount of etching front by dividing up the total area to be lifted into smaller areas. Channels are cut into the total area of material to be lifted thereby exposing the release layer. These channels can completely separate the area or can consist of slits cutting part way into the liftoff area.

Figure 10A:
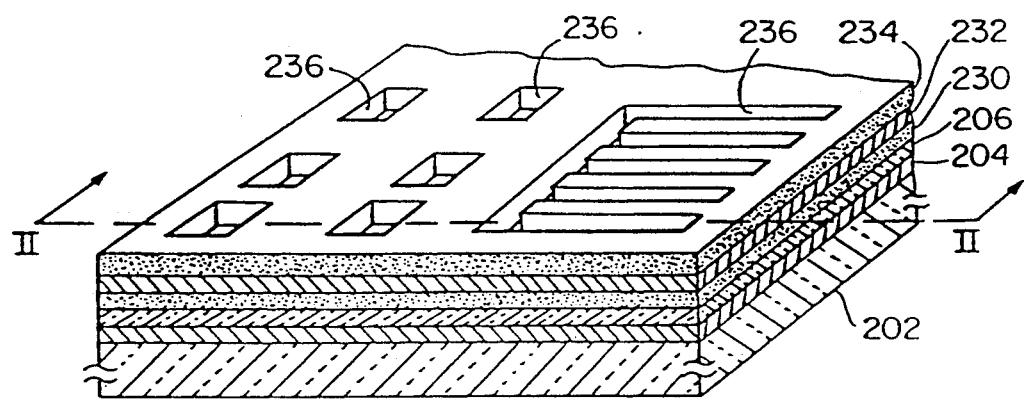
FIG. 10A is a partial perspective view of a wafer during lift-off processing according to another embodiment of the invention.
Figure 10B:
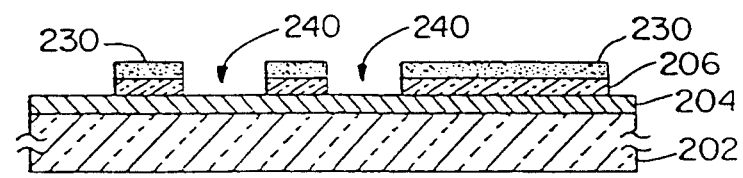
FIG. 10B is a sectional view taken along lines II—II of FIG. 10A of the lift-off structure after a step in the process.
Figure 10C:
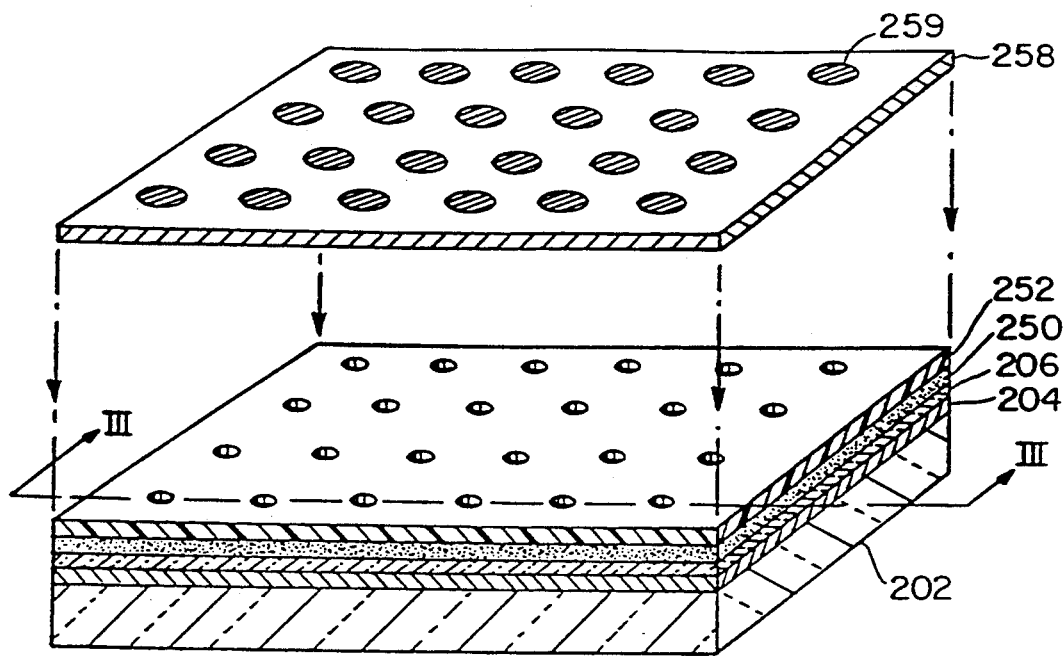
FIG. 10C is a partial perspective view of a portion of a wafer during lift-off processing in another embodiment where registration is maintained.
Figure 10D:
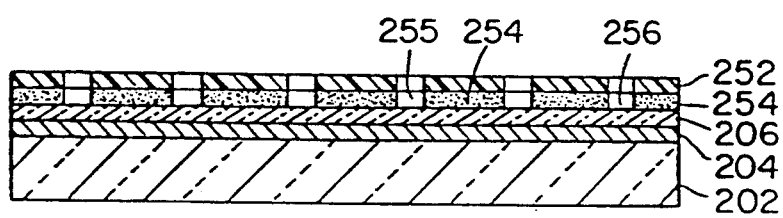
FIGS. 10D and 10E show cross-sections of the structure of FIG. 10C after additional steps in the lift-off process.
Figure 10E:
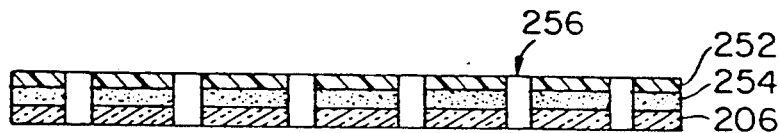

The second method addresses the problem of trying to register these small areas of material with respect to each other while at the same time allowing the etching medium greater access to the exposed release layer. The ability to do this allows for easy retrieval from the solution, wafer scale processing on the backside, and short lift-off times due to the smaller areas and maximum exposure of the etching front. The key feature of this approach is that it allows for registration of the entire wafer area while still providing the etching solution access to all the etching fronts.

Where registration between devices is required, as in an array of transistors, the lift-off method of the alternate embodiment of FIGS. 10C-10E offers many advantages.

This alternate process of FIG. 10C solves the difficult problem of trying to register small device or pixel areas of material with respect to each other, while at the same time allowing the etching medium access to the exposed release layer. The ability to do this allows for easy retrieval from the solution, wafer scale processing on the backside, and short lift-off times due to the smaller areas and maximum etching front. This approach also enables registration of devices throughout the entire wafer area while still providing the etching solution access to all the etching fronts. FIG. 10C, shows a rectangular partial section of a wafer. The wafer is formed of a semiconductor substrate 202 upon which a release layer 204 is deposited by CVD followed by a front processed transistor panel 206, all as previously described above.

Transformable material, such as uncured liquid UV epoxy 250 is spread onto the top or front surface of structure 206. The point of departure with the previous embodiment occurs in the next step, when a perforated planar grid 252, made of transparent material such as plastic, is aligned on top of the epoxy 250. The perforations 256 extend orthogonal to, and through, the plane of grid 252.

A photo-mask with opaque circles 256 aligned to cover the perforations 256 is then affixed over the grid 252 (FIG. 10C). (An optional UV transparent mask release layer (not shown) may be formed between the mask 258 and grid 252 to facilitate mask removal.) UV light is focused onto the mask, curing the underlying epoxy 254 everywhere except beneath the opaque circles 254, as shown in FIG. 10D wherein the cured sections of epoxy 250 are shown in shaded section and the uncured sections are in blank. The mask 258 is removed. The uncured epoxy 250 is removed from the openings 256 by a suitable solvent and structure 206 etched away through the openings down the the release layer 204. The release layer is then etched away using the opening 256, as provided above. Access for the etchant is thus achieved at many points across the wafer, resulting in an array being attached to grid 252 by cured epoxy 254 (See FIG. 10E).

Figure 11A:
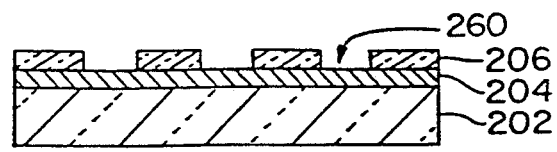
FIGS. 11A-11E are schematic drawings of a wafer during various steps in the process flow of a lift-off procedure in accordance with the invention.
Figure 11B:
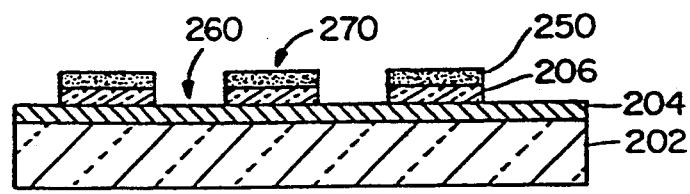
Figure 11C:
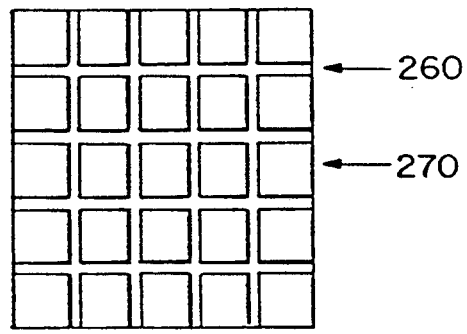
Figure 11D:
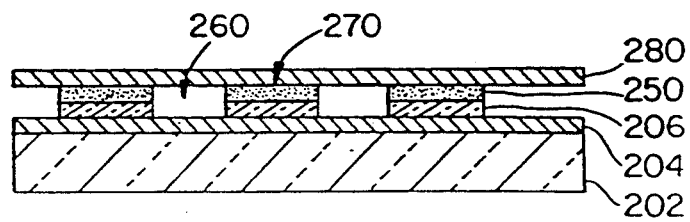
Figure 11E:
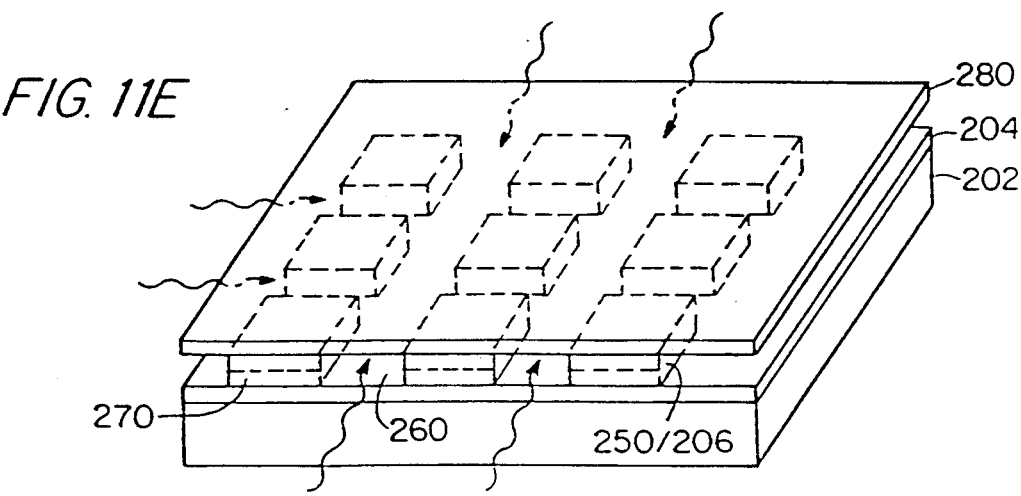

Another approach to registration is to form channels 260 directly in the device material by etching down to the release layer 204, thereby forming channels in the material alone (FIG. 11A). These channels can also be made taller by using the UV cured epoxy patterning method of FIG. 9 and then etching down to the release layer 204, (See FIG. 11B), or any other method that forms channels 260, or access streets between the areas 270 to be separated, as shown in the plan view of FIG. 11C. A support 280 can then be attached to the material 270 over the channels 260 and then the etchant can be allowed to run along the channels, thereby giving the etchant access to the center of the wafers (FIGS. 11D-11E). Taller channels can assist in speeding up the capillary action to achieve faster release. Other methods can also be used to speed along the movement of the etchant up the channels 260, including vacuum assistance, ultrasonic assistance, etc.

Along the same lines, channels 260 can be made in the device material to expose the release layer below. A porous material is then spun on, or otherwise formed or attached to the front surface. This material is rigid or semi-rigid when cured by UV, heat, or solvent treatment, etc., and therefore able to support the lifted film after separation from the substrate. The material is sufficiently porous to pass the etchant fluid without being attacked by the etchant. In this way, the etchant passes through the porous material and is given access to the release layer at its exposed points.

In another embodiment, the release layer etchant is brought in contact with the release layer before the overlying support structure is attached to the structure 206. For this process to work, channels 260 must be formed between devices or areas of material to be lifted for the etchant to be trapped in. The basic process is as follows: Channels 260 are formed between lift-off areas 206 which expose the release layer 204 on substrate 202. This can be done with any of the previously described methods which create channels between devices. A simple method which works very well is to form the channels directly in the material 206 by photoresist masking followed by etching down to the release layer 204. This forms channels 260 in the material which are equal to the height of the material above the release layer. Next, an etchant is placed on the surface of the layer to be lifted, or the wafer is submerged in the etchant. In either case, the channels 260 between the areas to be lifted 206 are filled with the etchant material. After this is done, the overlying support layer, which will also hold the registration after lift-off, is affixed to the front surface of the structure 206 by bonding methods described in detail herein. The overlying support is secured to the material 206 while the wafer is submerged or while the etchant is covering the front surface of the wafer and filling the channels. The support materials must be rigid enough that they do not fill in the channels that have been formed and thereby force the etchant out. A suitable support material can comprise glass, plastic or other optically transmitting substrate. This allows for a solid support medium that does not need etchant access holes in it, thus greatly simplifying the process.

The trapped etchant sufficiently dissolves the release layer 204 so that the thin film area 206 can be removed while being supported and registered by support with the backside exposed for further processing, i.e., formation of backside conductor metallization and bonding pads.

In addition to the support materials referenced above, UV release tapes, which are well known in the industry for handling small devices, have proven to be an excellent support choice for several reasons. These tapes have the property that when exposed to intense UV radiation, they lose most of their adhesion. In addition, moisture does not seem to effect the adhesive, and they can be applied with great success, even if submerged in liquid. These tapes can be used alone or in conjunction with a thicker support. This additional support should be formed of material which is transparent to UV radiation unless it is to be permanent and it should not be attacked by the etchant being used.

Figure 12A:
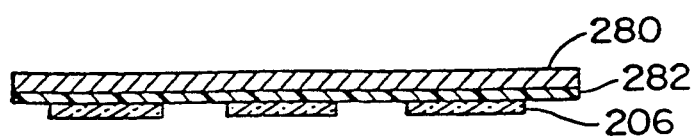
FIGS. 12A-12C are schematic sectional drawings of another preferred lift-off procedure of the invention.
Figure 12B:
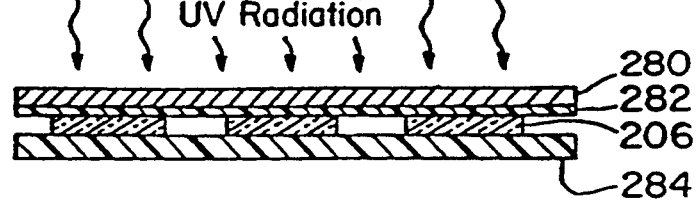
Figure 12C:
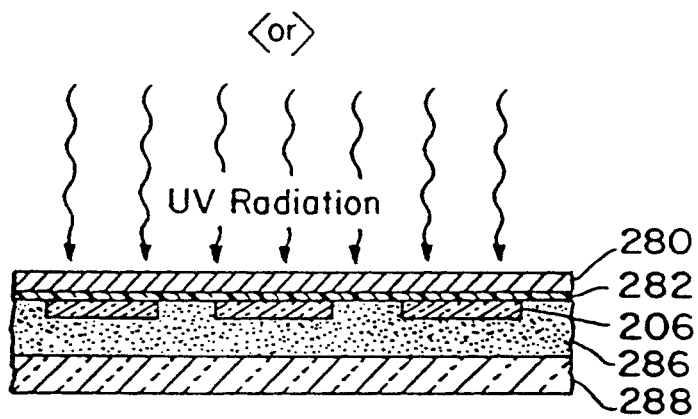

The UV release adhesive can be applied directly to other support materials, instead of the tape backing material. As shown in FIGS. 12A-12C, support 280, combined with double-sided UV release tape 282, can be used. One side of the tape 282 is adhered to the support. Then the other side is adhered to the front of the structure 206 after the etchant is applied. The etchant is then allowed to undercut the device 206. The devices are then attached by release tape to the support 280, as shown in FIG. 12A. The lift-off time is very short because the etchant has access to the release layer from many points on the wafer surface.

In this way, the devices are registered with respect to each other and are supported by the support 280 during backside processing.

The tape's adhesion can then be released by UV irradiation through the support (FIGS. 12B or 12C) and the tape can be taken off the carrier 280 with the devices still attached. Further UV exposure will decrease the adhesion of the devices to the tape to a sufficient degree to allow the devices to be removed by vacuum wand or to be transferred directly from the tape to any other tape 284 or epoxy 286 with substrate 288 (See FIGS. 12B or 12C) or other medium. Separate areas as large as 0.5 cm in width have been lifted by this non-curvature method. Total wafer size, which can be lifted and registered simultaneously, is only limited by the wafer size.

As indicated, an alternative embodiment involves use of UV-cured adhesive tapes and epoxies. The adhesive can be used to bond the thin-film transistors and CMOS circuit elements to glass. The adhesive is applied to plates that are as large, or larger than, 14"×14". Application methods include: spin coating, vapor coating, spraying, and standard thick film application processes to provide the necessary uniformity and optical quality.

Another preferred embodiment includes a method to transfer tightly placed devices to positions not so tightly spaced on the circuit panel. The technique illustrated in FIGS. 13A, B and C uses stretching or contracting of a stretchable tape or film until the devices are positioned correctly. This technique can also include previously described lift-off procedures and mechanical or a combination of stretching and mechanical methods. Commercially available devices can be used to precisely control the stretching of the film. Various methods can be used to measure the spacing of devices during stretching and transfer to provide proper registration of components.

Figure 13A:
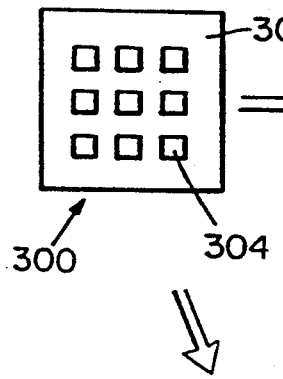
FIGS. 13A-13C schemztically illustrate a preferred method of transfer in accordance with the invention.

As illustrated in FIG. 13A in connection with structure 300, an array of transistors or thin-film semiconductor regions 304 has been transferred onto a stretchable substrate 302. Transistors or regions 304 have been fabricated and transferred in accordance with the procedures set forth above, or using any other suitable procedure. Substrate 302 can comprise an adhesive.

Figure 13B:
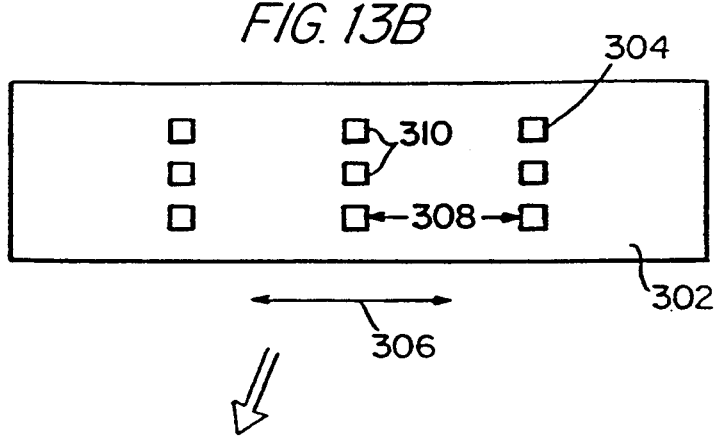

In a first embodiment the structure is stretched along axis 306, as shown in FIG. 13B, thereby increasing the distance 308 between devices 304 along axis 306 while leaving the distance 310 between devices in another direction the same. The substrate 302 is then stretched along axis 314 to produce the array shown in FIG. 13C where devices 304 have spacing 308 in one direction and spacing 312 in an orthogonal direction.

Figure 13C:
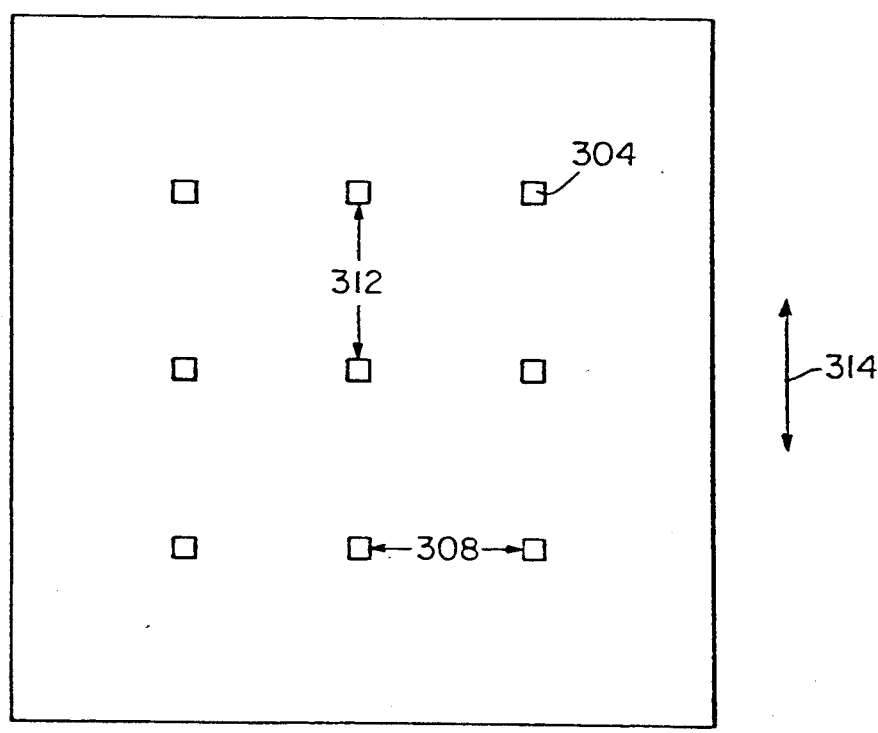

In another embodiment the structures 300 of FIG. 13A is stretched simultaneously in directions 306 and 314 to provide the array shown in FIG. 13C.

Figure 14A:
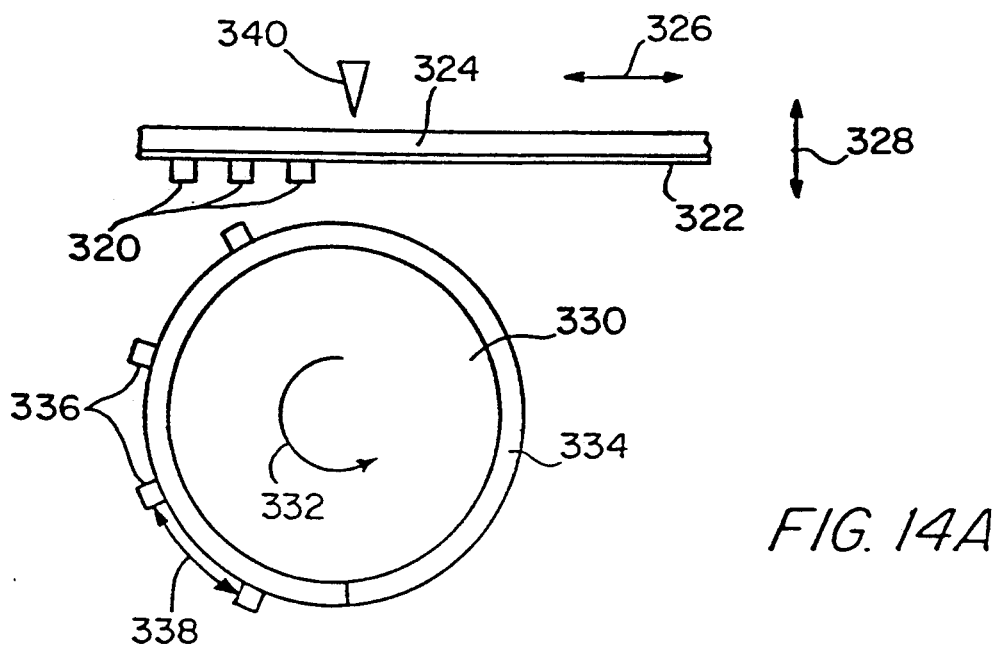
FIGS. 14A and 14B schematically illustrate additional transfer methods in accordance with the invention.
Figure 14B:
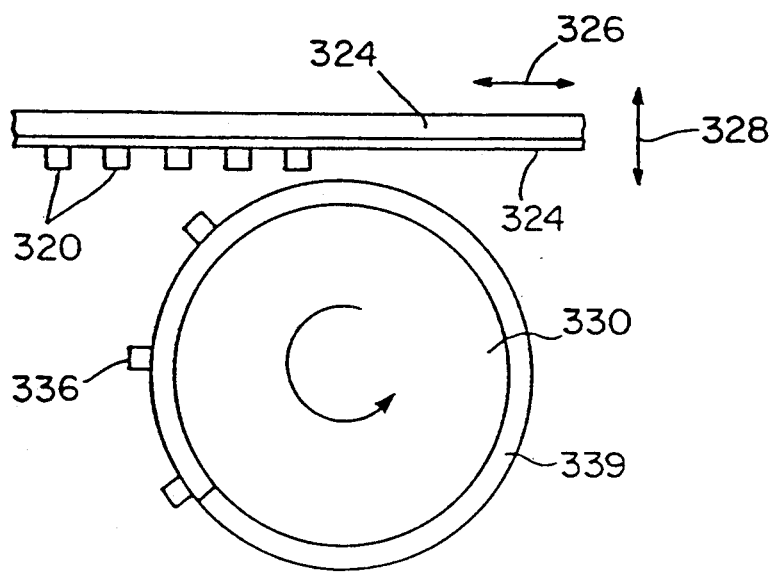

A mechanical technique is shown in FIGS. 14A and B. One starts with a lifted off array of devices 320 on a tape. This tape 322 is placed on a frame 324 that moves in and out along axis 326 and up and down along axis 328. A drum 330 with a flexible tape 334 is placed around its circumference. A instrument 340 is then pushed onto the device 324, pushing the first row of devices onto the drum tape 334. The drum tape 334 is indexed in direction 332 at the necessary angle and again the instrument 340 pushes a second row of devices with spacing 338 onto the tape 334. This continues until all the rows are transferred. This first drum tape 334 with the rows of devices 336 is then put onto frame 324. The same operation continues by transferring rows onto a new drum tape 339.

Another embodiment is to stretch the tape in one direction, transfer this to another tape and stretch that tape in the other direction and transfer the devices to the final support. This method is well-suited for small disconnected devices.

Figure 15:
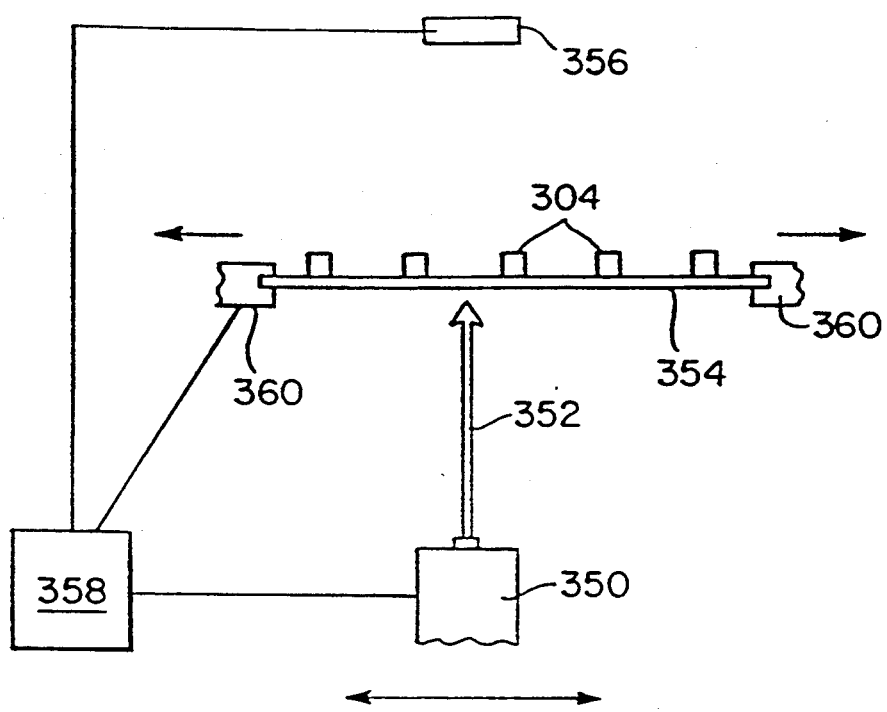
FIG. 15 illustrates a preferred system for monitoring and controlling device registration in accordance with the invention.

A system for measuring the distance between devices 304 on a transfer or final substrate is shown schematically in FIG. 15. A laser 350 directs a beam 352 in the direction of substrate 354 and scans across the source. Sensors 356 are positioned to detect transmitted and/or reflected light an generate signals where the beam is deflected by a device 304. A controller 358 correlates movement of the beam 352 relative to the substrate 354 so that the distance between the devices 304 is accurately measured. Controller 358 is electrically connected to stretching mechanism 360 so that adjustments can be made to the spacing of selected rows or columns of devices.

Stretching mechanism 360 can consist of a piston that is pressed through a collar to which the substrate 354 is attached. The movement of the piston face against substrate 354 and through the collar stretches substrate 354 in a precisely defined manner to increase the spacing between devices 304.

Alternatively, there are commercially available stretching mechanisms like that shown in FIG. 15 which grip the substrate along its periphery and precisely pull the substrate in the appropriate direction.

After stretching the registered devices are transferred to glass, polyester or other suitable substrate for light valve (LCD) fabrication. Alternatively, the devices can be mounted onto light emitting devices for display fabrication.

Figure 16:
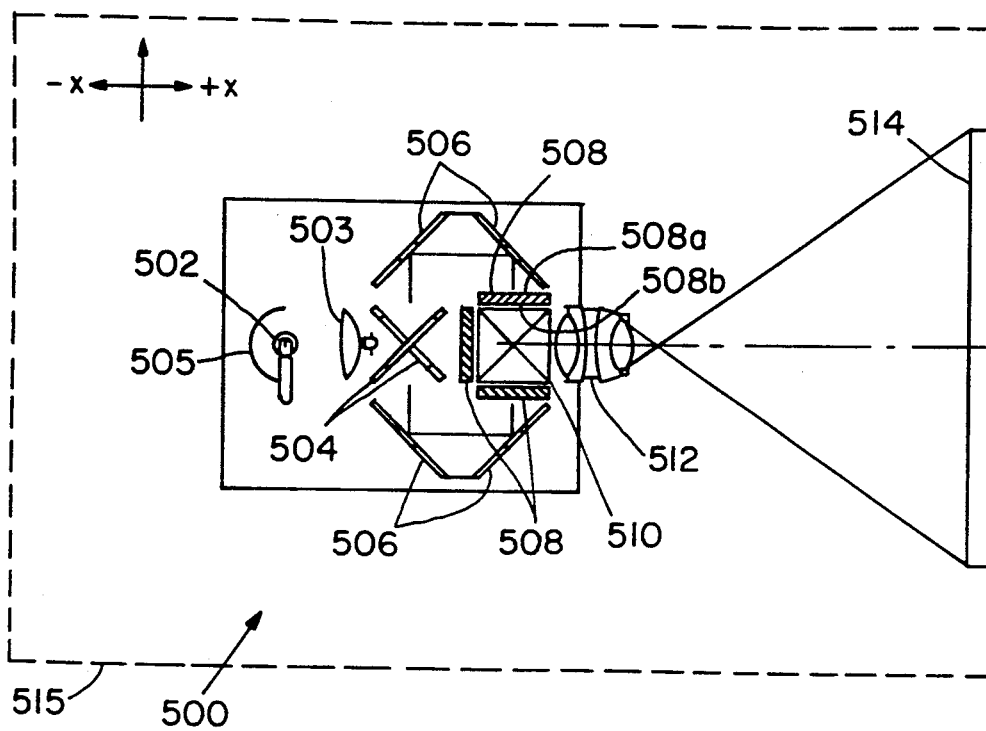
FIG. 16 is a cross-sectional view of a preferred projection system employed in a high resolution monitor of the present invention.

In another preferred embodiment of the present invention is a projection monitor which is shown in FIG. 16. The projection monitor includes a projection system 500 which produces multi-color images that are ultimately directed to an enlarged surface 514 which maybe a projection screen, a mirror, or lens. While a direct path from the projection system 500 to the surface 514 is shown in FIG. 16, in preferred embodiments the image output from the projection system is passed through an optical geometry before being projected onto the surface 574. Cooling can be provided by a fan or a suitable heat sink.

Within the projector, light from a halogen lamp 502 is directed by a reflector 505 and a condenser lens 503 to a crossed pair of dichroic mirrors 504. The condenser lens 503 is preferably designed for maximum collection efficiency to collect light emitted in the +X direction. The spherical reflector 505 collects light emitted in the −X direction and images the light of the lamp back onto itself.

White light from the lamp 502 is directed to the crossed dichroic mirrors 504 which separate the light into red, green and blue primary color portions. The separated colors of light are directed by adjacent mirrors 506 to illuminate the back side 508a of each of three liquid crystal light valve matrices 508. In accordance with the present invention, each light valve matrix 508 comprises an array of transistors, an array of electrodes, polarizers, cover glass, and drivers formed in a thin film of substantially single crystal silicon and an adjacent liquid crystal material through which light is selectively transmitted to the surface 514 (described in detail below).

Each light valve matrix 508 is controlled by a driver circuit for modulating the individual light valves so that the illuminating light may be selectively transmitted through the liquid crystal material to form an image in the respective primary color at the front side 508b of the matrix. The three primary color images are then optically combined by a dichroic prism 510 into a single multi-color light beam. The light beam is projected by a projection lens 512 to the surface 514.

In another preferred embodiment, the projection system employs a single light valve matrix modulated to produce a monochrome light beam which is projected onto the enlarged surface. In yet another preferred embodiment, each light value matrix employs a ferroelectric material through which light is selectively transmitted to a viewing surface for display.

Figure 19:
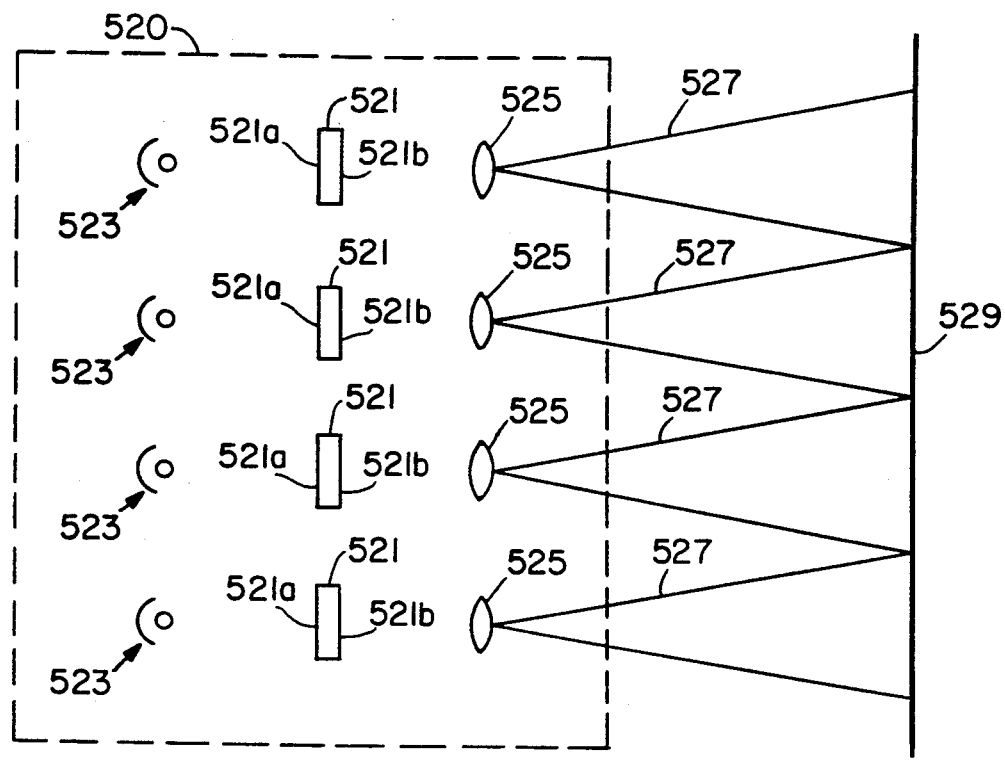
FIG. 19 is an illustration of another preferred projection system which may be employed in the monitor of FIG. 18.

Although a preferred projection system has been described with three light valve matrices and a particular internal optical geometry, preferred embodiments may include one or more light valve matrices configured with various internal optical geometries. For example, in one preferred embodiment a high resolution composite image can be produced in a projection system 520 having four or more light valves arranged with individual optics. Referring to FIG. 19, four light valve matrices 521 each provide an N×N pixel array. Light from each light source 523 is directed to illuminate the back 521a of a respective matrix 521. Each light valve matrix is controlled by a drive circuit (not shown) for modulating the individual light valves (or pixels) so that the illuminating light may be selectively transmitted through the liquid crystal material within the matrix to form an image at the front side 521b of the matrix. Note that each matrix 521 may be capable of producing monochrome or multi-color images.

Each image, which is preferably compatible with 35 mm optics, is directed to a respective lens 525. Each lens provides a light beam 527 which is projected onto a portion of the surface 529. As such, each matrix is configured to provide an image segment of the composite image. Using this configuration, a composite high resolution image having a pixel density of N×4N is produced. The composite image may then be displayed onto a screen or directed through an optical geometry for display.

Figure 20:
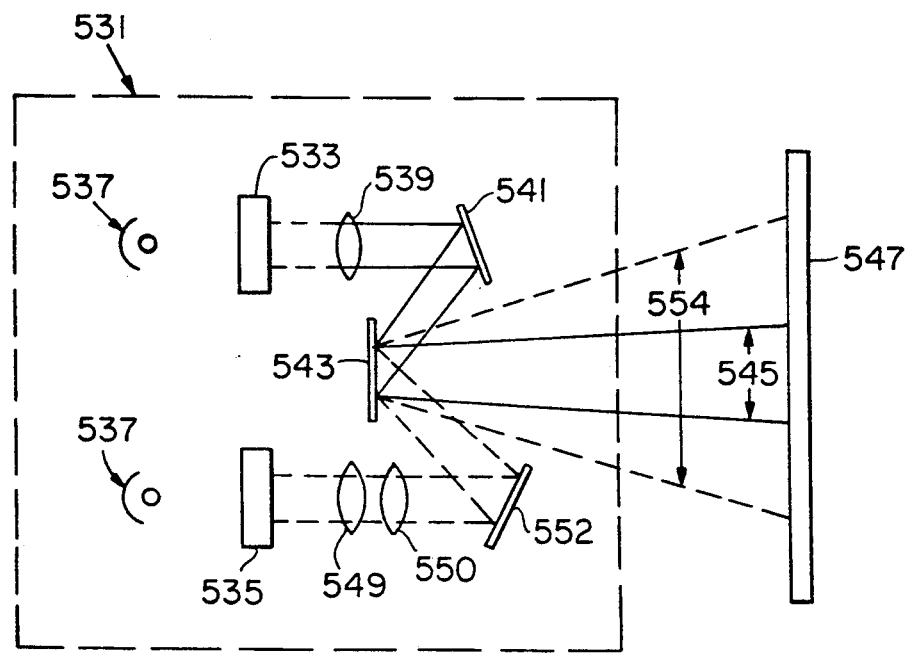
FIG. 20 is an illustration of another preferred projection system which may be employed in the monitor of FIG. 18.

In another preferred embodiment, a pair of light valve matrices are employed with an optical arrangement in a projection system to provide high resolution images. Refering to FIG. 20, a pair of light valves matrices 533 and 535 are positioned in a projection system 531. Light from light sources 537 is directed to illuminate the back of the respective matrices. Each matrix 533 and 535 is controlled by a drive circuit (not shown) and may produce monochrome or color images. The image formed at the front side of each matrix is directed to a respective lens system. More specifically, the image produced by the matrix 533 is directed by focal lens 539 to a pair of mirrors 541 and 543. The image reflects off the mirror 541 as well as another mirror 543 and is projected onto the center area 545 of the surface 547. Similarly, the image produced by the matrix 535 is directed by lenses 549 and 550 to the mirrors 552 and 543. However, the mirror 552 is arranged such that the image, reflected off mirror 552 and mirror 543, is projected onto a large area 554 of the surface 547. The two images reflecting off of the mirror 543 combine to produce, a high resolution center area 545 and a lower resolution periphery 554 on the surface 547.

Figure 21:
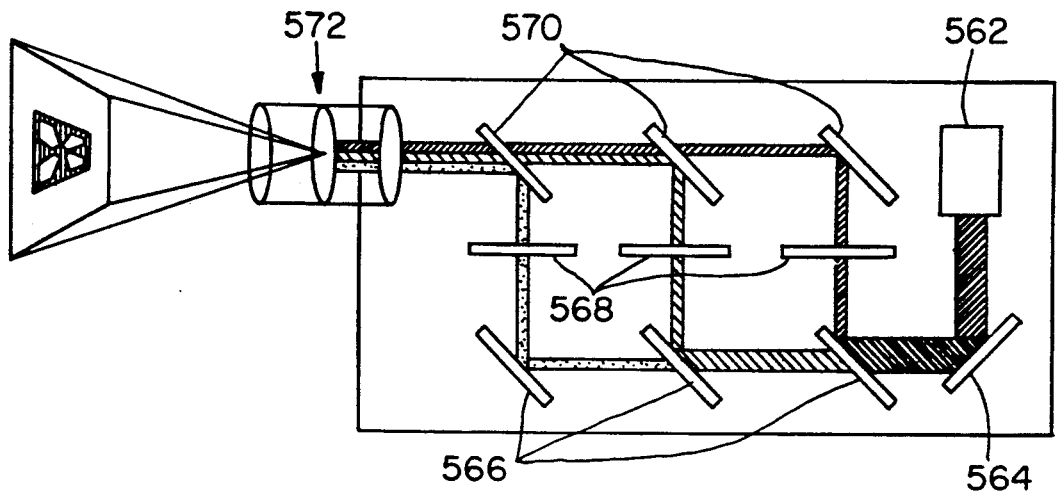
FIG. 21 is an illustration of an image projector of the present invention.

An image projector 560 employing the principles of the present invention is shown in FIG. 21. The projector employs a zoom or variable focus lens 572 for projecting images to a viewing surface (not shown). By replacing the zoom lens 572 with a simple lens, the projection system within the projector can be employed in the monitor of FIG. 17. The projection system of FIG. 21 employs yet another optical configuration for directing light. White light from a lamp 562 is reflected off a mirror 564 and directed to three dichroic mirrors. The separated colors of light are directed by the mirrors to illuminate the back side of three liquid crystal light valve matrices 568. Each matrix, controlled by a driver circuit (not shown), selectively transmits light to form an image in the respective primary color at the front side of the matrix. The three primary color images are directed via dichroic mirrors 570 to lens 572. The lens combines the images into a single multi-color light beam.

Figure 17:
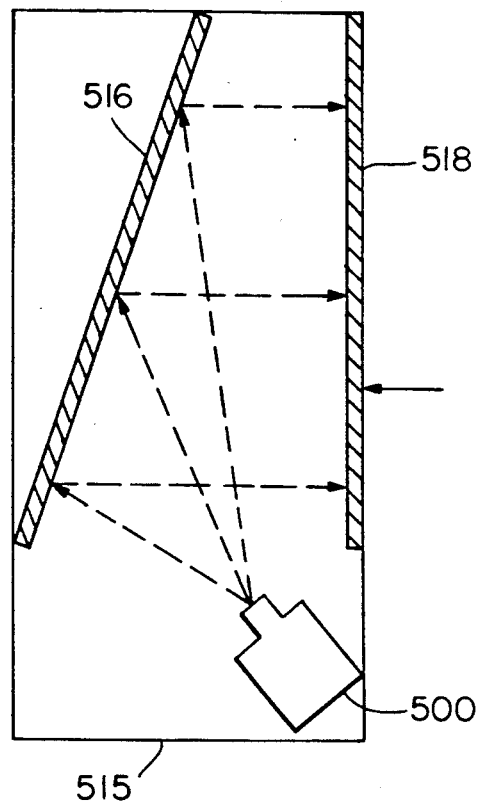
FIG. 17 is an illustration of a preferred high resolution monitor of the present invention.
Figure 18:
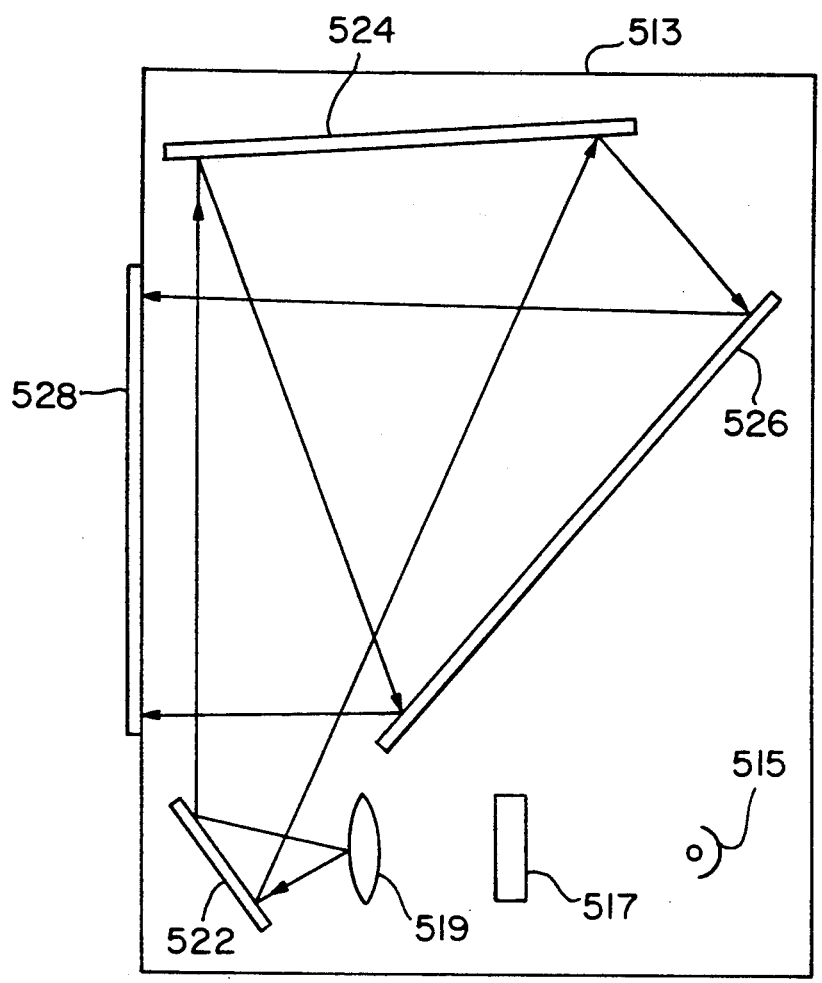
FIG. 18 is an illustration of a high resolution projection monitor which employs a folded optics geometry.

Refering to FIG. 17, the projection monitor 515 includes an optical arrangement for directing the light beam from the projector to a screen 518. To that end, the projection system 500 projects a monochrome or multi-color light beam to a mirror 516. The mirror is positioned at angle relative to the projection system such that light reflecting off the mirror is collimated. The collimated light is directed to the back side of a large viewing screen 518. As such, images may be viewed at the front side of the screen 518.

Figure 22:
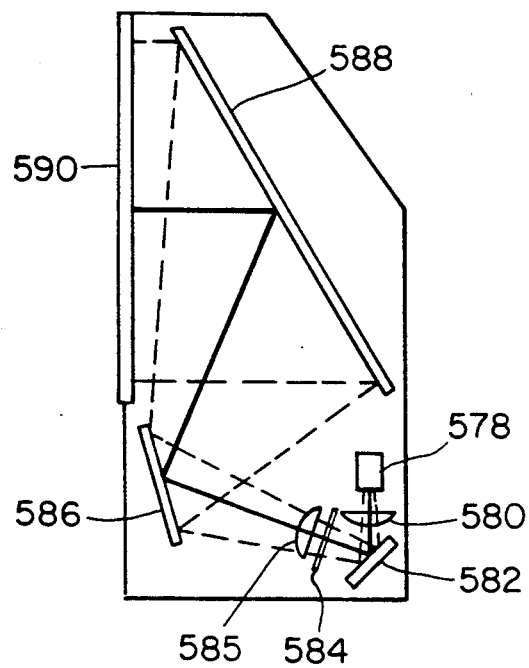
FIG. 22 is an illustration of another preferred high resolution projection monitor of the invention.

Another projection device incorporating the principles of the present invention is a projection monitor shown in FIG. 22. For simplicity of illustration purposes, a single light valve matrix and a supporting optics geometry is shown; however, preferred embodiments include plural light valve matrices each having a supporting optics geometry. With reference to FIG. 22, a light source 578 generates white light which is directed by a lens 580 to a mirror 582. The dichroic mirror 582 separates the white light into a single primary color and directs the colored light to the light valve matrix 584. The light is selectively transmitted through the matrix forming a image which is directed by lens 585 to a folded optical arrangement of mirrors. As such, the image is directed to a first mirror 586 which in turn directs the image to a second mirror 588. The second mirror is positioned such that light reflecting off of it is collimated. The collimated single color image is combined with other single color images and the resulting collimated image is directed to the back side of a large viewing screen 590. As such, high resolution images may be viewed at the front side of the screen.

Yet another projection device incorporating the principles of the present invention is the stand-alone projector 560 shown in FIG. 21. As explained previously, the projector 560 employs a plurality of single crystal silicon light valve matrices and an optical geometry for producing high resolution color (or monochrome) images. The resulting images are directed through a zoom or variable focal length projection lens 572 to form an image beam capable of being front or back projected onto a viewing surface or screen. As in previous embodiments, the projector provides high resolution images while being compatible with 35 mm optics.

Figure 23:
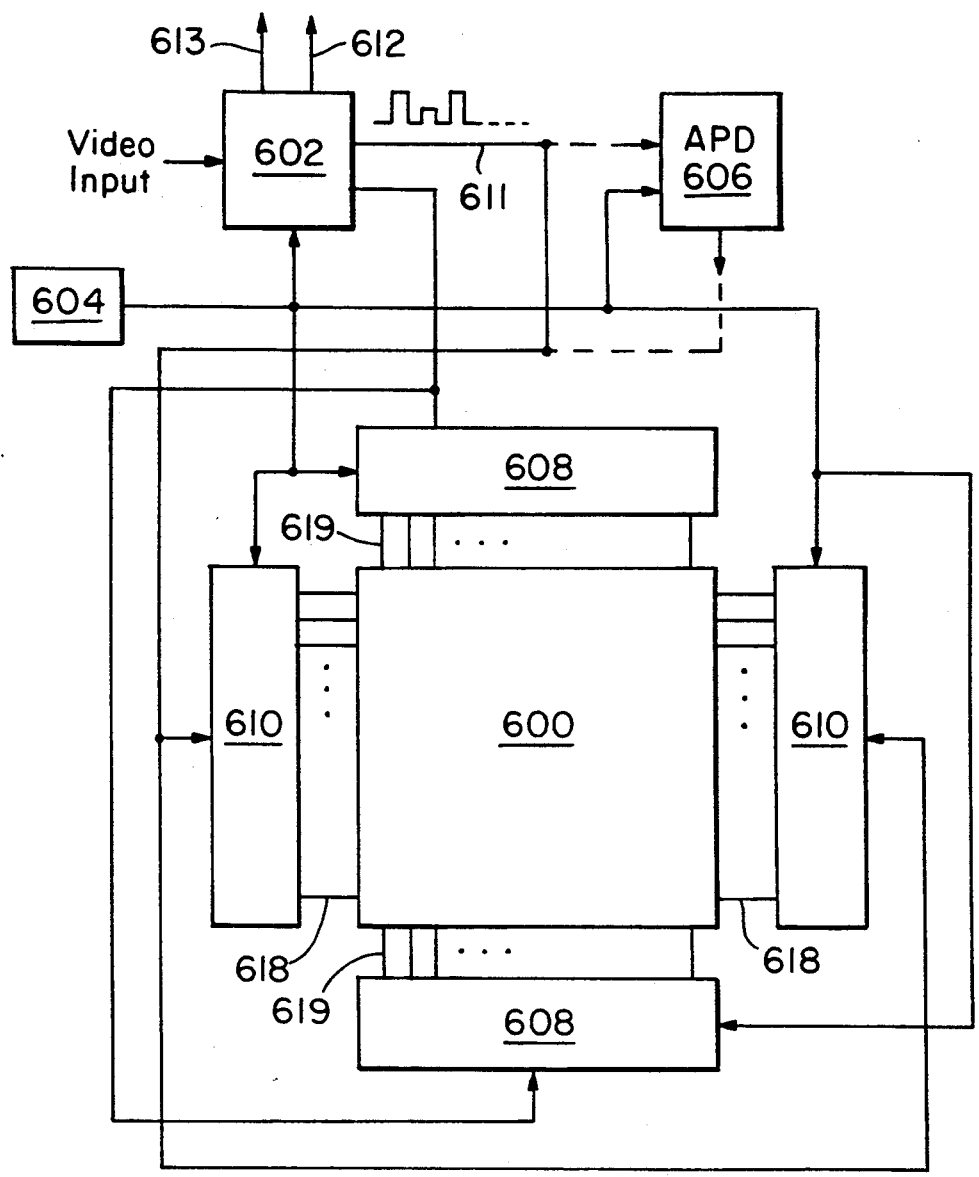
FIG. 23 is a circuit diagram illustrating the driver system for a projection device of the present invention.

Preferred embodiments of the projection display devices include a driver circuit for driving one or more light valve matrices. Referring to FIG. 23, an active matrix 600 comprises a plurality of light valves which are individually actuated by colocated driver circuitry (see FIG. 1B). The colocated driver ciruitry is controlled by supporting driver circuitry which includes a video conditioning circuit 602, a system clock 604, an optional amplitude to pulse duration (APD) converter 606, column drivers 608, and a row drivers 610.

The video conditioning circuit 602 receives a video input signal which may be an RGB signal, an NTSC signal or other video format signal, or any digital or analog signal. The conditioning circuit processes the incoming signal producing separate video output signals (on lines, 611, 612 and 613) for each primary color and a synchronization signal (on line 615) for the column and row drivers 608 and 610. The video output signal on line 611 is a serial data stream wherein the amplitude of each signal of the data stream determines the intensity of light transmitted through each light valve.

If the APD convertor is not employed, the serial data stream on line 615 is received by the row drivers 610. The row drivers 610 send each of the signal data streams to the light valves through buses 618. The column drivers receive the sync signal on line 615 and, responsive to the sync signal, will be sent through buses 619 to turn on individual transistors allowing the associated signal of the data stream to charge the capacitor in each pixel. The capacitor sustains a charge, which is proportioned to the amplitude of the associated signal, on the light valve until the next scan of the array.

Alternately, the ADP converter may be employed such that each signal of the video output data stream is converted to a pulse having a pulse width which is proportional to the signal's amplitude. In any case, the driver circuit operates in the same manner as previously described.

Projection display devices of the present invention can employ light valve matrices having pixel densities which satisfy any of a wide range of the following existing computer display format requirements:

| Application | Display Format (Column × Row) |
| --- | --- |
| 1) Common Personal Computer | 1024 × 768 |
| | 1280 × 1024 |
| 2) Workstation (Advanced Personal Computer) | 1280 × 1024 |
| | 1580 × 1280 |
| | 2048 × 2048 |
| 3) Other Workstations (Non-Standard) | 1152 × 900 |
| | 1280 × 1024 |
| | 1600 × 1280 |

Thus, a display monitor employing one or more single crystal silicon light valve matrices having any of the above-described pixel densities may be provided in accordance with the present invention.

One feature of the present invention is that projection devices employing single crystal light valve matrices provide high resolution images. High resolution images are possible because high density light valve arrays may be formed in single crystal silicon films. Referring to Table 1, the light valve diagonal is shown for various array sizes and pixel densities. Note that the diagonal dimensions followed by an asterisk indicate the array is compatible with 35 mm optics.

The use of 35 mm optics is a key feature in minimizing the size, weight and cost of the described optics requiring the light valve image designed dimension to be no greater than 42 mm (1.654 inches). Therefore, it is desirable to use a light valve imaging technology that provides the highest density of information content. It is likely that the light valve technology discussed herein is compatible with as-fabricated densities of 2000 dots-per-inch. This allows projection of high resolution images using compact, low cost and widely available optical components. The small size of the light valve allows the use of small format condenser lens assembly dichroic mirrors and prisms and projection lens. Subsequently, the package size of the described projector and monitor can be maintained at small dimensions and component weight is similarly minimized. Appropriate 35 mm format optical components are widely available and can be obtained at low cost relative to large and/or custom optical components. For projector and monitor requirements that cannot be met with a 35 mm compatible light valve, larger conventional or custom optical components may be employed. Due to the minimum size of a particular light valve format afforded by the described light valve technology, similar cost, size and weight advantages are translated to the procurement of custom optical components.

As has been described, the light valve technology described herein can be used to implement projection arrays of 1024×768 through 2048×2048 pixels using 35 mm format optical components. This will permit the execution of high resolution color and monochrome image projectors and monitors at relatively compact dimensions and low weight.

One implementation of the monitor is to form a 17.5 inch×11.5 inch image suitable for the display of two side-by-side 8.5 inch×11 inch pages with additional screen room for data window access. The use of the described light valve and projection technology would allow the physical format of the monitor to be less than 22 inches high, less than 20 inches wide, and less than 10 inches deep. The use of a single 150 to 300 watt metal-halogen lamp in this implementation would provide the rear-proporation screen image at a brightness of 25 foot-Lamberts or greater. The choice of screen material could include a simple diffuser for maximum viewing angle or a lenticular configuration for maximum brightness over a reduced solid viewing angle.

TABLE 1

| DIAGONAL ARRAY DIMENSION - INCHES/(MM) Fabricated dots/inch (DPI) on light valve matrix | | | | |
| --- | --- | --- | --- | --- |
| ARRAY SIZE | 800 | 1000 | 1200 | 2000 |
| 1024 × 768 | 1.600* | 1.280* | 1.137* | 0.640* |
| | (40.64) | (32.51) | (28.88) | (16.26) |
| 1280 × 1024 | 2.049 | 1.639* | 1.366* | 0.820* |
| | (52.04) | (41.63) | (34.70) | (20.82) |
| 1580 × 1280 | 2.542 | 2.033 | 1.695 | 1.017* |
| | (64.56) | (51.65) | (43.05) | (25.82) |
| 2048 × 2048 | 3.620 | 2.896 | 2.414 | 1.448* |
| | (91.96) | (73.57) | (61.32) | (36.78) |

Another feature of the present invention is that a projection display device employing single crystal silicon light valve matrices provides images with high brightness. To accomplish this, each single crystal silicon light valve matrix employed in a projection display device has a high optical aperature which is defined as the percentage of transparent area to total matrix area. Table 2 provides the optical aperature for various light valve arrays. It is noted that in general the minimum acceptable optical aperature for an array is 40%. As indicated by Table 2, as pixel density increases, which increases image resolution, optical aperature decreases. However, reducing the switching device size and/or the interconnect size for a given pixel density will increase the optical aperature.

TABLE 2

| OPTICAL APERTURE COMPUTATIONS | | | | |
|---|---|---|---|---|
| Transistor length (um) | 3 | 3 | 3 | 3 |
| Transistor width (um) | 6 | 6 | 6 | 6 |
| Line width (um) | 2 | 4 | 6 | 8 |
| lines per inch | 1000 | 1000 | 1000 | 1000 |
| pixel size (um) | 25.4 | 25.4 | 25.4 | 25.4 |
| grid shadow (sq. um) | 97.6 | 187.2 | 268.8 | 342.4 |
| trans. shadow (sq. um) | 18 | 18 | 18 | 18 |
| pixel area (sq. um) | 645 | 645 | 645 | 645 |
| Packing Factor (%) | 85 | 85 | 85 | 85 |
| OPTICAL APERTURE (%) | 69.8 | 58.0 | 47.2 | 37.5 |
| Transistor length (um) | 3 | 3 | 3 | 3 |
| Transistor width (um) | 6 | 6 | 6 | 6 |
| Line width (um) | 2 | 4 | 6 | 8 |
| lines per inch | 800 | 800 | 800 | 800 |
| pixel size (um) | 31.8 | 31.8 | 31.8 | 31.8 |
| grid shadow (sq. um) | 123 | 238 | 345 | 444 |
| trans. shadow (sq. um) | 18 | 18 | 18 | 18 |
| pixel area (sq. um) | 1008 | 1008 | 1008 | 1008 |
| Packing Factor (%) | 85 | 85 | 85 | 85 |
| OPTICAL APERTURE (%) | 73.1 | 73.1 | 73.1 | 73.1 |
| Transistor length (um) | 3 | 3 | 3 | 3 |
| Transistor width (um) | 6 | 6 | 6 | 6 |
| Line width (um) | 2 | 4 | 6 | 8 |
| lines per inch | 1200 | 1200 | 1200 | 1200 |
| pixel size (um) | 21.2 | 21.2 | 21.2 | 21.2 |
| grid shadow (sq. um) | 80.7 | 153.3 | 218.0 | 247.7 |
| trans. shadow (sq. um) | 18 | 18 | 18 | 18 |
| pixel area (sq. um) | 448 | 448 | 448 | 448 |
| Packing Factor (%) | 85 | 85 | 85 | 85 |
| OPTICAL APERTURE (%) | 66.3 | 52.5 | 40.2 | 29.5 |
| Transistor length (um) | 3 | 3 | 3 | 3 |
| Transistor width (um) | 6 | 6 | 6 | 6 |
| Line width (um) | 2 | 4 | 6 | 8 |
| lines per inch | 2000 | 2000 | 2000 | 2000 |
| pixel size (um) | 12.7 | 12.7 | 12.7 | 12.7 |
| grid shadow (sq. um) | 46.8 | 85.6 | 116.4 | 139.2 |
| trans. shadow (sq. um) | 18 | 18 | 18 | 18 |
| pixel area (sq. um) | 161.3 | 161.3 | 161.3 | 161.3 |
| packing Factor (%) | 85 | 85 | 85 | 85 |
| OPTICAL APERTURE (%) | 50.9 | 30.4 | 14.2 | 2.2 |

Figure 24A:
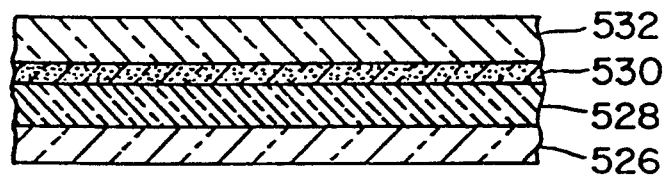
FIGS. 24A-24D are a preferred process and transfer sequence for fabricating a light valve matrix and transferring it to a support structure.

In another preferred embodiment, a growth and transfer process is employed to provide a thin-film of single crystal silicon positioned on glass as shown in FIGS. 24A-24D. Referring to FIG. 24A, a buffer (insulator) layer 528 of silicon is epitaxially grown on a silicon substrate 526. A strained GeSi layer 530 is epitaxially grown on the buffer layer 528 and an upper layer 532 of single crystal silicon is epitaxially grown on the GeSi layer. The strained layer 530 should be thin, on the order of a few hundred angstroms, to avoid misfit defect formation that would thread into the upper silicon layer 532.

Figure 24B:
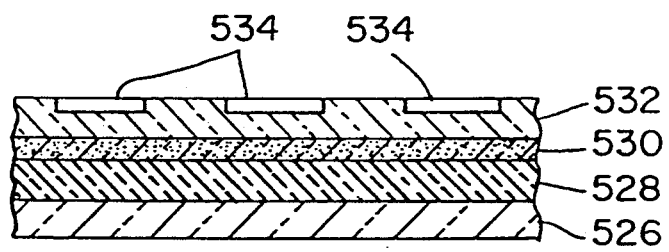
Figure 24C:
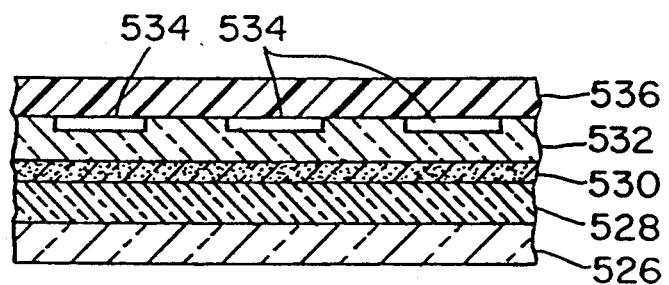
Figure 24D:
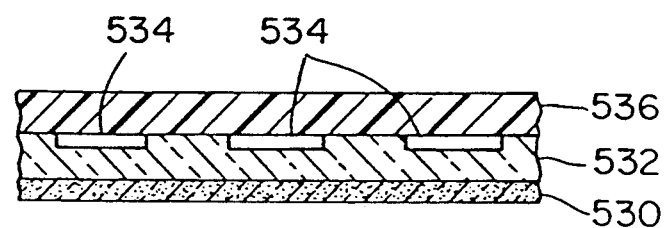

Referring to FIG. 24B, integrated circuit processing techniques, such as any of the techniques previously described herein, are employed to form light valve matrix circuitry 534 in the single crystal silicon layer 532. Next, the processed wafer is mounted with an epoxy adhesive of the type described below to a glass or plastic support 536 (FIG. 24C). The epoxy fills in the voids formed by the processing and adheres the front face to the support 536. The silicon substrate 526 and buffer layer 528 are etched off with the GeSi layer 530 serving as an etch stop layer (FIG. 24D). The GeSi layer could then be selectively etched away without effecting the silicon film 532.

FIGS. 25A-25C illustrate another preferred process for transferring and adhering circuits of thin films of silicon to a glass substrate. The starting structure is a silicon wafer 718 upon which an oxide layer 716 and a thin film of poly-Si, a-Si or x-Si 714 is formed using any of the previously described processes such as ISE or CLEFT. A plurality of circuits, such as pixel electrodes, TFT's, Si drivers and Si logic circuits, are then formed in the thin film. FIG. 25A shows three such wafers, A, B, C. In wafer A, logic circuits 740 are formed. In wafer B, pixel electrodes 762 and TFT's 751 are formed. In wafer C, driver circuits 720 are formed. A wafer is attached to a superstrate transfer body 712, such as glass or other transparent insulator, using an adhesive 721. Preferably the adhesive is comprised of an epoxy, such as, a cycloaliphatic anhydride; for example; for example, EP-112 LS made by Masterbond Inc. The adhesive must satisfy the following criteria:

Excellent spectral transmission in the visible range;
Good adhesion to glass, oxides, metals, nitrides;
No reactions with glass, metals, oxides, nitrides;
Low shrinkage;
Low warp/stress;
Able to tolerate acids or bases at 100° C. for extended periods without lifting, losing adhesion, or degrading;
Able to withstand 180° C. for 2 hours with no optical change;
Good resistance to acids and solvents;
Able to tolerate dicing and heating step (including an acid etch step with no lifting);
Low viscosity to allow thin adhesive films; and
Ability to be vacuum degassed to eliminate all bubbles.

In general, the cycloaliphatic anhydrides meet most of the above criteria. The epoxy preferably has a low cure temperature to minimize shrinkage, a very low ion content ($\leq 5$ ppm) and spectral stability over extended time periods.

The wafer is attached, using the adhesive 721, to a glass superstrate 712. The adhesive is vacuum degassed to eliminate all bubbles. The sandwich structure is then cured at a low temperature of about 100° C. for 4-8 hours which causes the adhesive to gel and minimizes the shrinkage characteristics. Then the adhesive is fully cured at a higher temperature of about 160° C. for about 8 hours. This cure assures that the bonds are fully matured. Without this cure, the adhesive will not stand up to the subsequenct acid etching step.

The wafer, is then cleaned and the native oxide 718 is etched off the back surface. The wafer is put into a solution (KOH or equivalent) of 25 grams to 75 ml H2O at 100° C. Depending on the thickness of the wafer, it may take up to 5 hours to etch the Si 718 and oxide 716 layers. The solution etches silicon very rapidly, i.e. 2 to 3 microns/min., and uniformly if the wafers are held horizontally in the solution with the etching surface face up. The etchant has a very low etch rate on oxide, so that as the substrate is etched away and the buried oxide is exposed, the etching rate goes down. The selectivity of the silicon etch rate in KOH versus the oxide etch rate in KOH is very high (200:1). This selectivity, combined with the uniformity of the silicon etching, allows the observer to monitor the process and to stop the etch in the buried oxide layer 716 without punching through to the thin silicon layer 714 above it. Wafers up to 25 mils thick and oxides as thin as 4000 Å have been successfully etched using this process. An alternative etchant is hydrazine, which has a much higher etch rate selectivity or ethylene diamine pyrocatacol (EDP).

When the silicon is completely gone, the vigorous bubbling, which is characteristic of silicon etching in KOH, abruptly stops, signalling that the etching is complete.

The thin films 714 transferred to the respective glass superstrates 712 are now rinsed and dried. If not already provided with circuits 740, 751, 762, or 720, the films 714 can be backside circuit processed if desired, since the epoxy adhesive 720 has very good resistance to chemicals. In addition, the epoxy is very low in stress, so that the thin film is very flat and can go through conventional photolithography steps.

In the aforementioned light valve matrix fabrication processes, disclination defects in the liquid crystal material may be induced by non-planar circuit topography formed in the film resulting in irregular stacking and subsequent image aberration. Planarized circuitry would eliminate the disclination problem. An option is to use the oxide layer after transfer of the film to the optically transmissive substrate to provide a planar surface. The oxide layer is planar or substantially planar (i.e. uniformities of ≦1 microns across its surface) such that an even topography is provided. Then any necessary shielding or pixel circuitry can be formed to produce a planarized circuit substantially free of disclination.

In the aforementioned embodiments, it is noted that light valve matrices having a diagonal of 1-2 inches do not require spacers in the liquid crystal volume (see FIG. 1A). Since spacers are non-transmissive elements, eliminating them from the volume results in an improved optical aperture and thus increased brightness for the matrix. Also prevents optical aberation caused by spacers at small pixel geometries.

Due to the higher intensities of light used in projection systems that are necessary to provide the desired brightness, the sensitivity of the single crystal pixel transistors to the light source can impair performance. The light source can be a halogen lamp that produces between 100 and 1000 watts and preferably operates in the range of 150-300 watts. Other lights such as discrete lasers (RGB), cathodoluminescent light sources, and arc-lamps producing similar levels of power per unit area can also be used. It is therefore desireable to reduce the sensitivity of the active matrix to the light source. This is accomplished by shielding one or both sides of each transistor in the array with a light shield that will substantially attenuate the light directed or scattered toward each transistor. A metal or other optically opaque material can be used as a shield. When the shield is a metal it can also serve as an interconnect or a gate to the transistor being shielded. At normal incidence, a metal shield can completely attenuate light from the source at wavelengths at or above the silicon bandgap with thicknesses in the range of 2000-10,000 angstroms. Shielding can also be employed around the edge of the active matrix to attenuate or block light directed towards the peripheral circuitry.

Figure 26D:
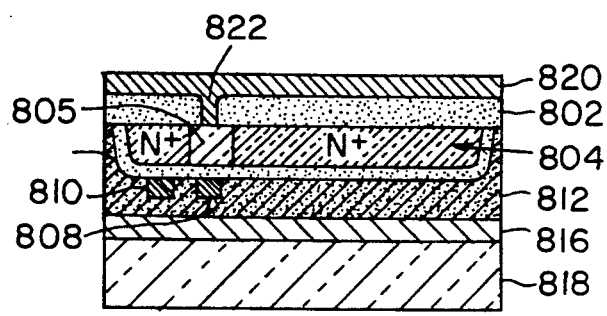
Figure 26E:
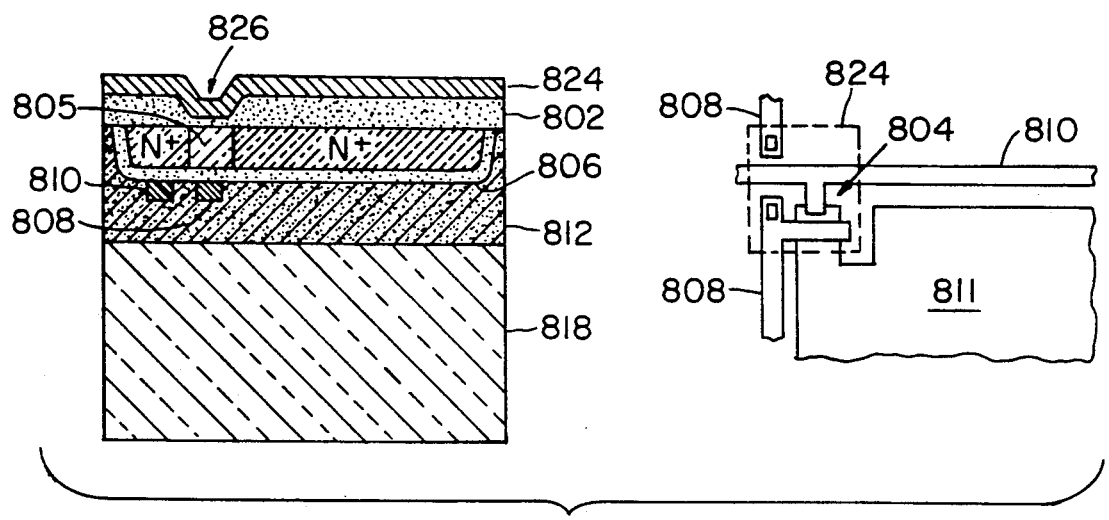

In FIGS. 26A-26E a process for fabricating a double shielded active matrix array for a projection system is illustrated. The left figure shows a cross-sectional view of a pixel transistor of each step or embodiment. The right side illustration in FIGS. 26A-26C and 26E show a top view including the transistor 804, pixel area 811, and interconnect lines 808 and 810. In FIG. 26A there is shown the silicon substrate 800, oxide layer 802, source and drain 804 regions, a channel region 805, a second oxide layer 806, and portions of the interconnect lines 808 and 810 that serve as the gate and source connector for the transistor 804. FIG. 26B shows a third oxide layer 812 and holes 814 formed therein to provide a bridge interconnect between portions of line 808. In FIG. 26C is shown the formation of the first metal shield 816 over the oxide 812 and through holes 814 to interconnect lines 808. The first shield 816 has a surface area to substantially block normally incident light from reaching transistor 804 from one side of the circuit panel. The area of shield 816 should be minimized to maintain the optical aperture of the array. FIG. 26D illustrates the use of a body contact 822 fabricated after the transfer of the panel onto glass substrate 818 and formation of the second shield 820. The fabrication of such a body contact is described more fully in U.S. Ser. No. 07/823,858 filed on Jan. 22, 1992, which is incorporated herein by reference. In FIG. 26E there is illustrated the use of a portion of the second shield 824 as a second back side gate 826. Gate 826 can be used to control the opposite side of the channel from the front side gate region 808. The present transfer process thus provides for additional back side processing to provide optical interconnects, optical shielding interconnects, and double sided gating of each or selected transistors in the array.

The light valve image projector and monitor configurations can be used for the applications beyond image presentation. These include image generation/projection for electronic printing and photographic image recording. In the former, the light valve and image projection optics can be used to form an image on an electrophotographic media (as in the imaging drum of xerographic or laser printer processors). The key advantage is that the entire two-dimensional image can be exposed at once. For photographic applications, the image can be projected onto photographic film or paper.

Color can be implemented in the projector or monitor through the use of color filters instead of dichroic mirrors. In one implementation, white light from a single or multiple lamps could be passed through each of red, green and blue filter to its incidence onto the appropriate color-assigned light valve. Alternatively, color filters can be fabricated directly on the light valve assembly. This could be done with a single color filter (e.g., red, green or blue) on a light valve or the specific allignment of color filters on the discrete elements constituting the light valve. The latter would allow a color image to be obtained using a single light valve but forces a factor of 3 or 4 reduction in color pixel density as the elements are assigned a red, green, or blue filter or a red, green blue and white filter respectively. Alternatively, subtractive color filters (yellow, cyan and magenta) would be similarly used.

A key criterion in the projector/monitor design is the management of heat generated by the lamp light source. A significant portion of this heat is in the form of infrared (IR) radiation eminating from the lamp. Methods of controlling this IR radiation are its absorption by an IR filter or its reflection by an IR "heat mirror" that allows high transmission of visible light to the subsequent optics. Another method is the use of a dichroic mirror that separates the IR radiation from the visible light path and directs the IR to directly exit the projector or monitor housing.

A light valve panel formed by the described technology is compatible with 35 mm format optics. Therefore, this imaging device can be fabricated such that the assembled device has equivalent physical dimensions as a standard 35 mm photographic transparency whose image is projected via a conventional and generally available 35 mm "slide projector". Thus, an embodiment of the light valve projector is to use a single light valve matrix panel with integral drive electronics, as described herein, that is packaged to be size equivalent with a standard mounted 35 mm transparency and insert this modular electronic imaging device into a 35 mm "slide projector" without modification in order to generate the projected image. The light valve imaging device is connected by a cable to control electronics as are described herein. In this embodiment, a single light valve panel could generate a monochrome image or a color image through the use of applied color filters as described elsewhere herein. The light valve panel used for this embodiment can have the same fabricated element/pixel density as described for the other embodiments.

Figure 27:
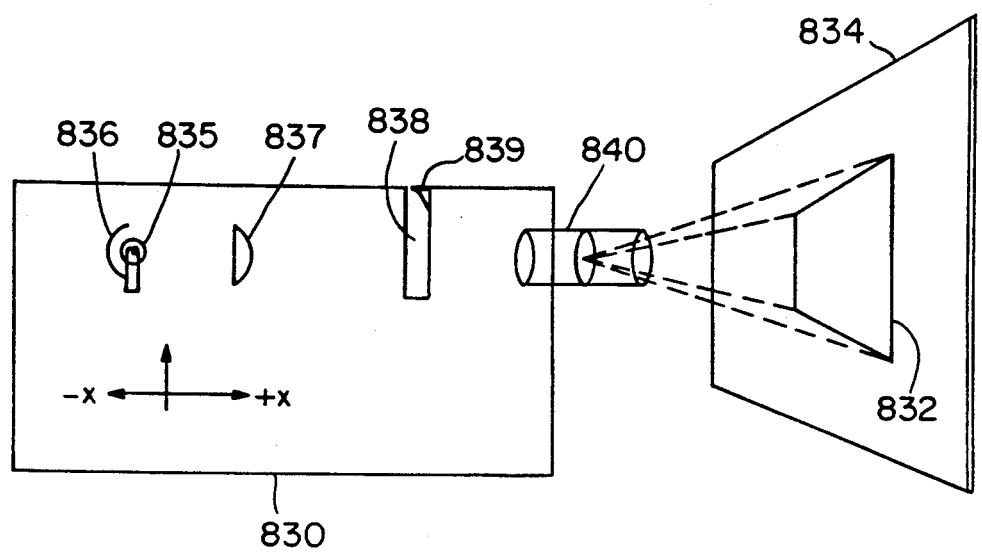
FIG. 27 is an illustration of a conventional slide projector.

Accordingly, other preferred embodiments of the present invention are directed to an active matrix (AM) slide assembly adapted for use in a conventional 35 mm slide projector for providing monochrome or multi-color images. A conventional slide projector is illustrated in FIG. 27. The projector 830 produces from slide transparencies monochrome or multi-color images 832 that are projected to an enlarged surface 834 which may be a projection screen or any relatively flat surface.

Within the slide projector 830, light from a halogen lamp 835 is directed by a reflector 836 and an optional condenser lens 837 to slide chamber 838. The spherical reflector 836 collects light emitted in the −X direction and images the light of the lamp back onto itself. The condenser lens 837 is preferrably designed for maximum collection efficiency for collecting light emitted in the +X direction. The white light from the lamp 836 is directed to a slide transparency (not shown) positioned in the slide chamber 838. The illuminating light is manipulated as it passes through the slide, producing an image which is directed to an optical system 840. The image is projected by the optical system 840 to the surface 834.

Figure 28:
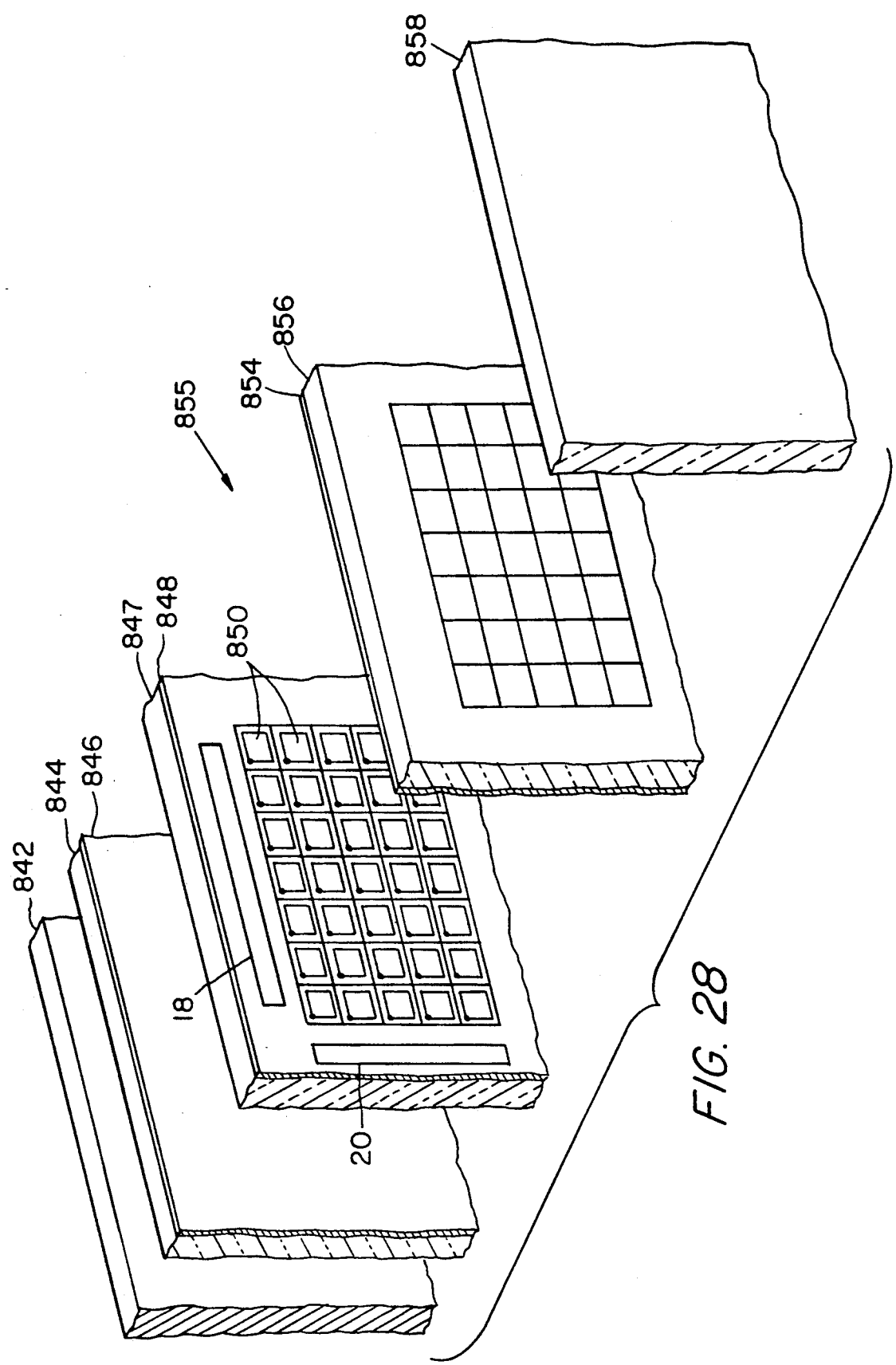
FIG. 28 is an exploded perspective view of an active matrix slide assembly in accordance with the present invention.

In accordance with the present invention, the active matrix slide is adapted to be securely positioned in the slide chamber for selectively transmitting light from the lamp to provide monochrome or multi-color images to the optical system for projection onto a viewing surface. A preferred embodiment of an active matrix slide is illustrated in FIG. 28. The basic components of the AM slide include a first polarizing filter 842, a glass substrate 844, a transparent and conductive ITO coating 846, an epoxy adhesive 847, an active matrix circuit panel 848, a second transparent and conductive ITO coating 854, a glass superstrate 856 and a second polarizing filter 858. These components are arranged in a layered structure and secured in a slide housing (shown in FIG. 29A) dimensioned to fit securely in a 35 mm slide projector chamber. It is noted that the side walls of the housing, the ITO coatings and the superstrate provide electrical shielding for the active matrix circuitry. A liquid crystal material (not shown) is placed in a volume 855 between the circuit panel 848 and the glass superstrate 856.

An important feature of the active matrix slide of the present invention is that it is compatible with existing slide projectors. Referring to FIG. 27, the slide chamber 838 of an existing projector 830 is dimensional to accept a standard 2×2 inch slide having a thickness of up to ⅛ths of an inch. Since a standard 35 mm slide usually has a significantly smaller thickness. a spring-loaded slide holder 839 is provided to secure the slide in the chamber. In accordance with the present invention, an active matrix slide has a 2×2 inch face with a thickness of less than about ⅛ths of an inch such that it can be securely positioned in a slide chamber without modification thereto.

As explained previously with respect to other embodiments, the active matrix circuit panel 848 has an array of pixels or light valves 850 which are individually actuated by a drive circuit. The drive circuit includes first 18 and second 20 circuit components that are positioned adjacent the array and electrically connected to the light valves for modulating the individual light valves so that the illuminating light may be selectively transmitted through the liquid crystal material to form a monochrome or multi-color image.

As noted above, the active, matrix circuitry can be adapted to provide color images through the use of color filters. In one embodiment, while light from the projector light source can be passed through each of a stacked arrangement of red, green and blue filters to the appropriate color assigned light value. Alternatively, a color filter can be fabricated directly onto each light valve and the light valves are arranged by filter color to provide uniform color images. For example, pixels can be arranged in a triad arrangement where three color filters are employed or the pixels can be arranged in a quad arrangement where four filters are employed.

In preferred embodiments, the active matrix circuit panel circuitry is formed in or on a layer of a semiconductor material such as silicon. It is noted that any number of fabrication techniques can be employed to provide preferred thin-films of polysilicon or single crystal silicon. In embodiments in which the active matrix is formed in a thin-film of single crystal silicon, any of the previously mentioned pixel densities can be provided such that high resolution images are produced. Other preferred embodiments employ the use of a solid state material or any material whose optical transmission properties can be altered by the application of an electric field can be used to supply the light valves for the AM slide of the present invention.

The drive circuit that can be used to control the pixels is illustrated in FIG. 1B. Circuit 18 receives an incoming signal and sends a signal to the pixels through buses 13. Circuit 20 will scan through buses 19 to turn on the individual transistors 23 which charges capacitor 26 in each pixel. The capacitor 26 sustains the charge on each pixel electrode and the liquid crystal 21 until the next scan of the array. The various embodiments of the invention may, or may not, utilize capacitors with each pixel depending upon the type of slide desired.

Figure 29A:
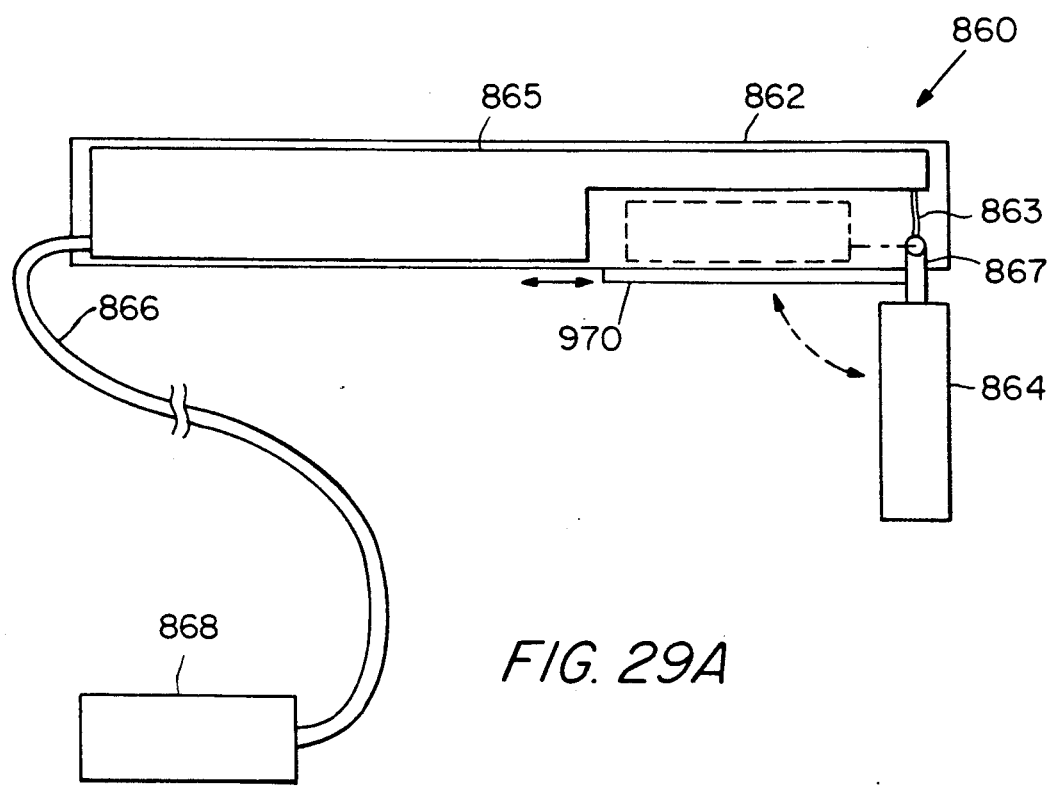
FIGS. 29A-29B illustrate a preferred embodiment of an active matrix slide assembly employed in a conventional slide projector.
Figure 29B:
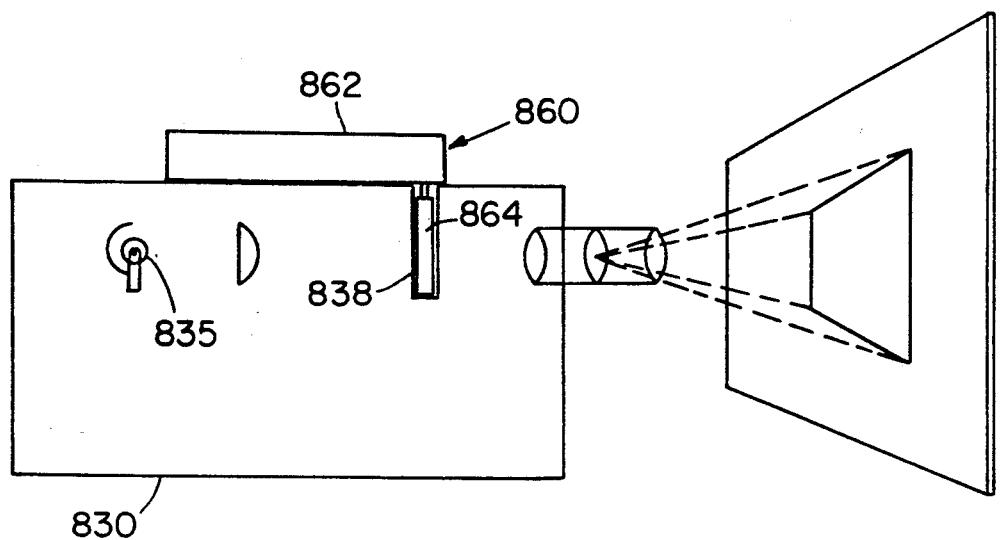

A preferred embodiment of an active matrix slide assembly for use with a slide projector is illustrated in FIGS. 29A-29B. Referring to FIG. 29B, the slide assembly 860 includes a housing 862 and an active matrix slide 864. The housing 862 is positioned on the slide projector 830 so that the slide assembly 860 is securely disposed in the slide chamber 838. Referring to FIG. 29A, the slide is rotatably mounted to the housing 862 by an arm 867. As such, the slide has a storage position (dashed lines) and an operating position. When the slide is rotated into the operating position, the sliding shielded cover 870 is moved into a closed position (as. shown) for sealing the housing.

The housing preferably contains a shielded electronics assembly 865 which is electrically connected to the slide by a cable 863. The electronics assembly 865 has an input cable (or connector) 866 for connecting to an image generation device 868 which may be a computer or any video device. Image data provided by the device 868 is processed by the electronics 865 and sent to the drive circuitry of the AM slide 864. Responsive to the received data, the drive circuitry modulates the individual active matrix light valves such that the illuminating light from the light source 835 is selectively transmitted through the slide to form monochrome or multi-color images.

Figure 30:
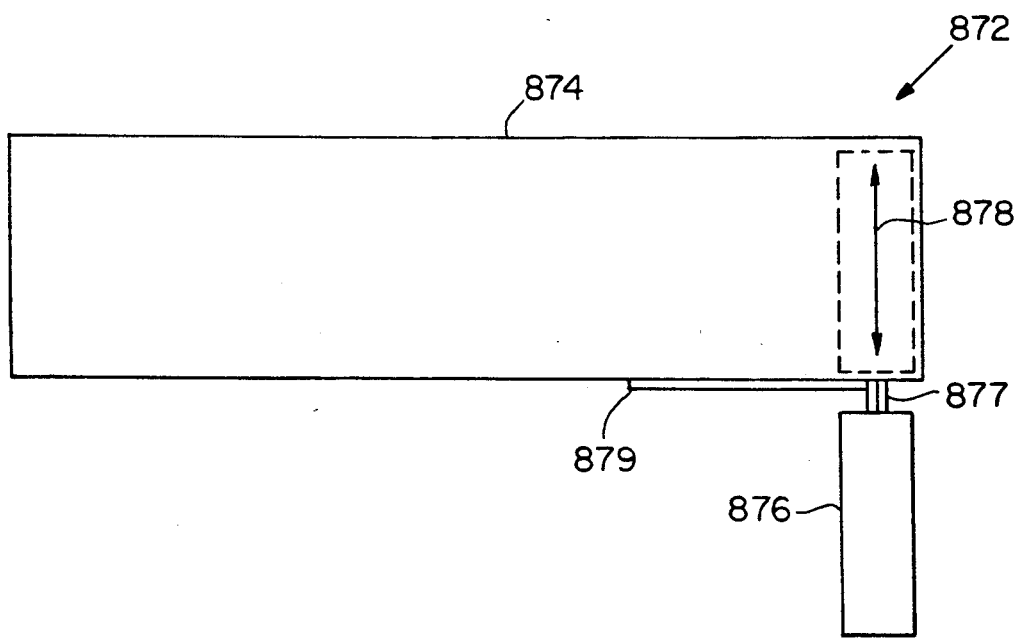
FIG. 30 is an illustration of another preferred embodiment of an active matrix slide assembly employed in a conventional slide projector.

Another preferred embodiment of an active matrix slide assembly is illustrated in FIG. 30. The slide assembly 872 includes an electronics housing 874 and an active matrix slide 876 translatably mounted to the housing by a spring-loaded arm 877. As such, the slide has a storage position (dashed lines) in the housing and an operating position located along a vertical axis 878. The slide 876 is moved into the operating position such that it can be positioned in the chamber of a slide projector (not shown). With the slide in the operating position, the shielded cover 879 is moved along an axis orthogonal to the vertical axis 878 into a closed position (as shown) for sealing the housing. Alternatively, a cover can be attached to arm 877 such that when the slide is moved to the operating position, the opening in the housing 874, through which the slide 876 is moved, is sealed by the cover. In another embodiment, the slide 876 is mounted on a track on the internal walls of housing 874 and is moved into the operating position by sliding along the track.

Figure 31:
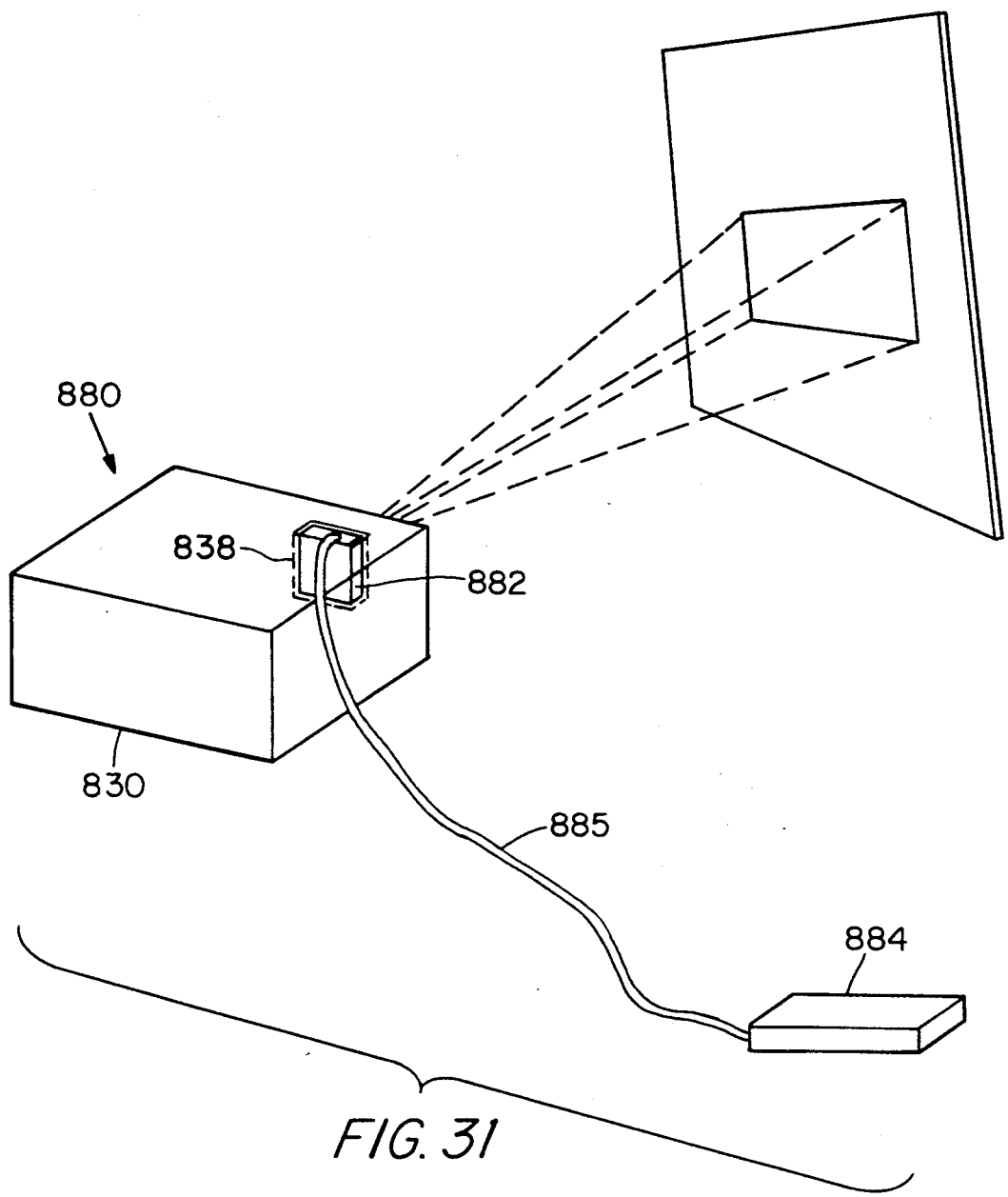
FIG. 31 is a perspective view of another embodiment of an active matrix slide assembly of the present invention.

In another preferred embodiment shown in FIG. 31, an active matrix slide assembly 880 includes an AM slide 882 and a remote electronics housing 884. The slide 882 is dimensioned to be securely positioned in the chamber 838 of the slide projector 830. The slide 882 is electrically connected to electronics in the remote housing 884 by a cable 885.

Figure 32:
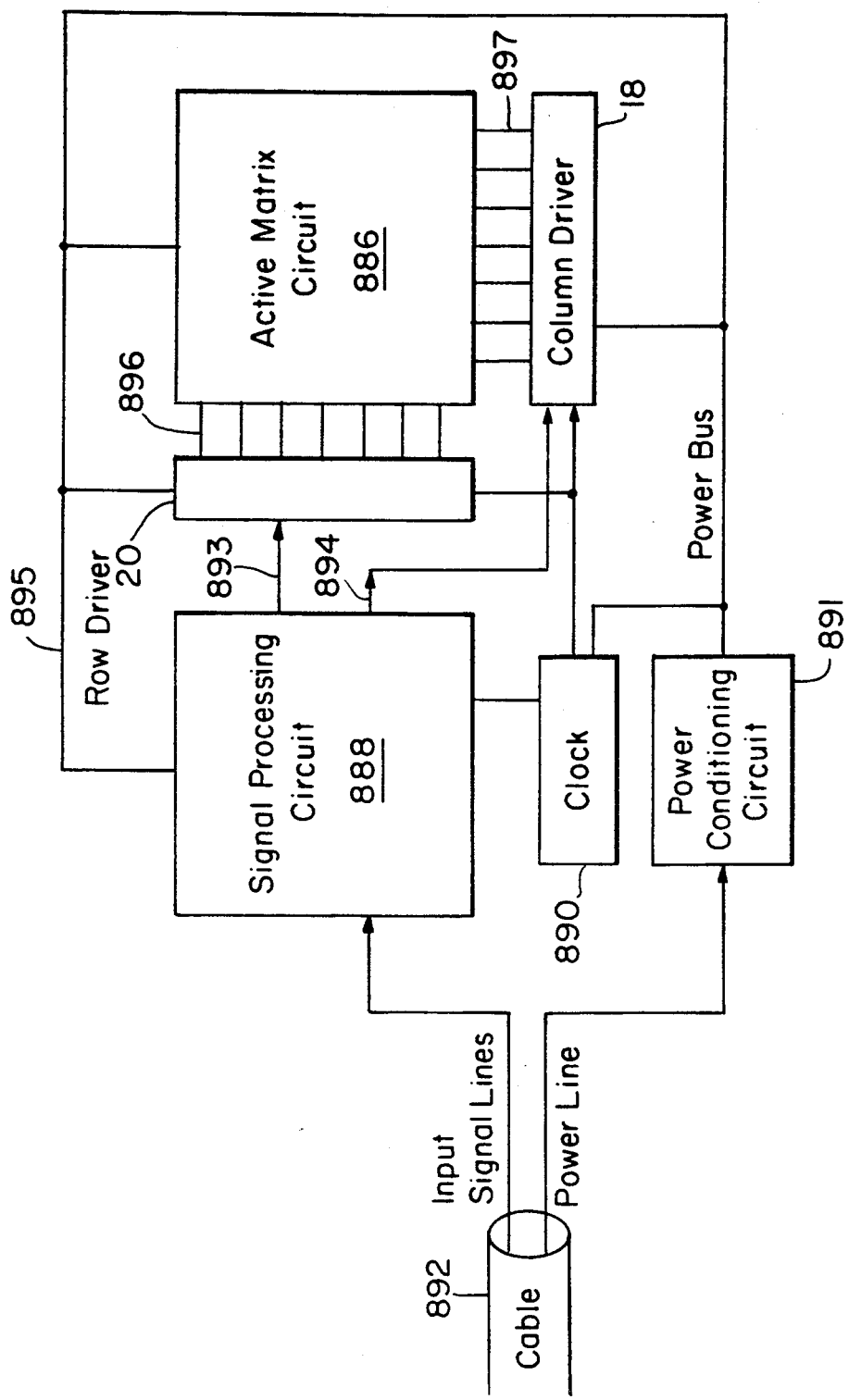
FIG. 32 is a circuit diagram illustrating a preferred driver system for an active matrix slide assembly.

As noted previously, preferred embodiments of the active matrix slide assembly (FIGS. 29A, 30 and 31) include a driver circuit for selectively actuating the active matrix light valves. Referring to FIG. 32, the active matrix 886 comprises a plurality of light valves which are individually actuated by colocated driver circuitry (see FIG. 1B). The colocated driver ciruitry is controlled by supporting driver circuitry which includes a signal processing circuit 888, a system clock 890, a power conditioning circuit 891, column drivers 18, and row drivers 20.

The signal processing circuit 888 receives via the cable 892 an input signal which may be an RGB signal, an NTSC signal or other video format signal, or any digital or analog signal. The signal processing circuit processes the incoming signal and (for a multi-color active matrix) produces separate video output signals for each primary color and synchronization signals for the column and row drivers. These signals are provided to the column driver (via bus 893) and row driver (via bus 894). The video output signal on line 895 is a serial data stream wherein the amplitude of each signal of the data stream determines the intensity of light transmitted through each light valve. Alternatively, the video output signal may be a digitally formatted data stream indicative of the light intensity.

The serial data stream on line 895 is received by the row drivers 18. The row drivers send each of the signal data streams to the light valves through buses 896. The column drivers 20, responsive to the sync signal, send a signal through buses 897 to turn on individual transistors allowing the associated signal of the data stream to charge the capacitor in each pixel. The capacitor sustains a charge, which is proportioned to the amplitude of the associated signal, on the light valve until the next scan of the array.

Figure 33:
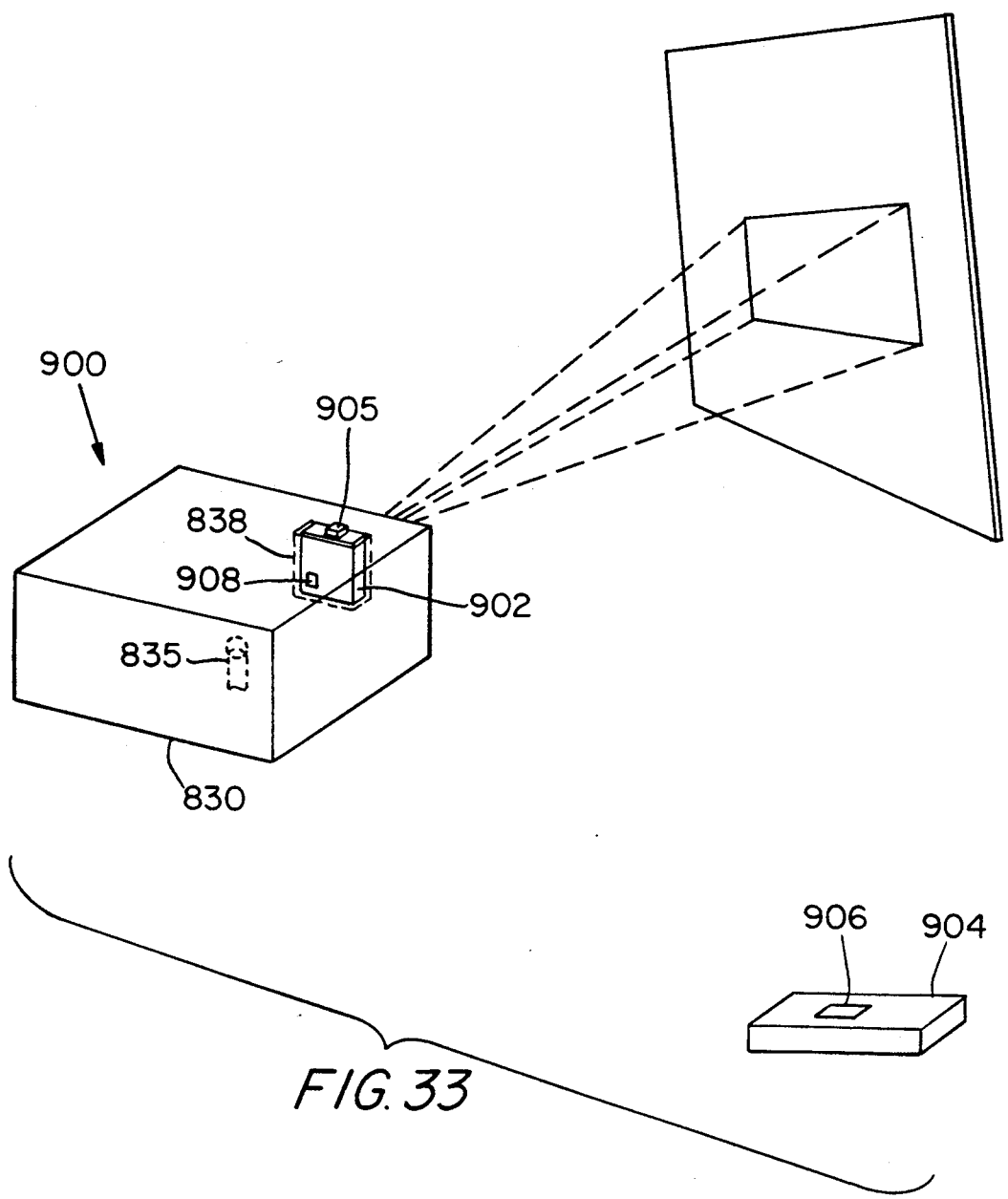
FIG. 33 is a perspective view of yet another embodiment of an active matrix slide assembly of the present invention.

In another preferred embodiment shown in FIG. 33, an active matrix slide assembly 900 includes an AM slide 902 and a remote electronics housing 904. The slide 902 is dimensioned to be positioned in the chamber 838 of a 35 mm slide projector 830. In contrast to previously-described embodiments, the slide 902 is not physically connected to the electronics housing 904. Instead, the slide and the electronics in the housing communicate with each other via antennas elements 905 and 906 respectively. In preferred embodiments, the antennas can be a pair of RF antennas or an infrared transmitter element such as an infrared LED paired with an infrared receiver element which can be a photodiode elements. The antenna 905 can be integrated into a handle (not shown) to provide for manual insertion and removal from chamber 838.

Figure 34A:
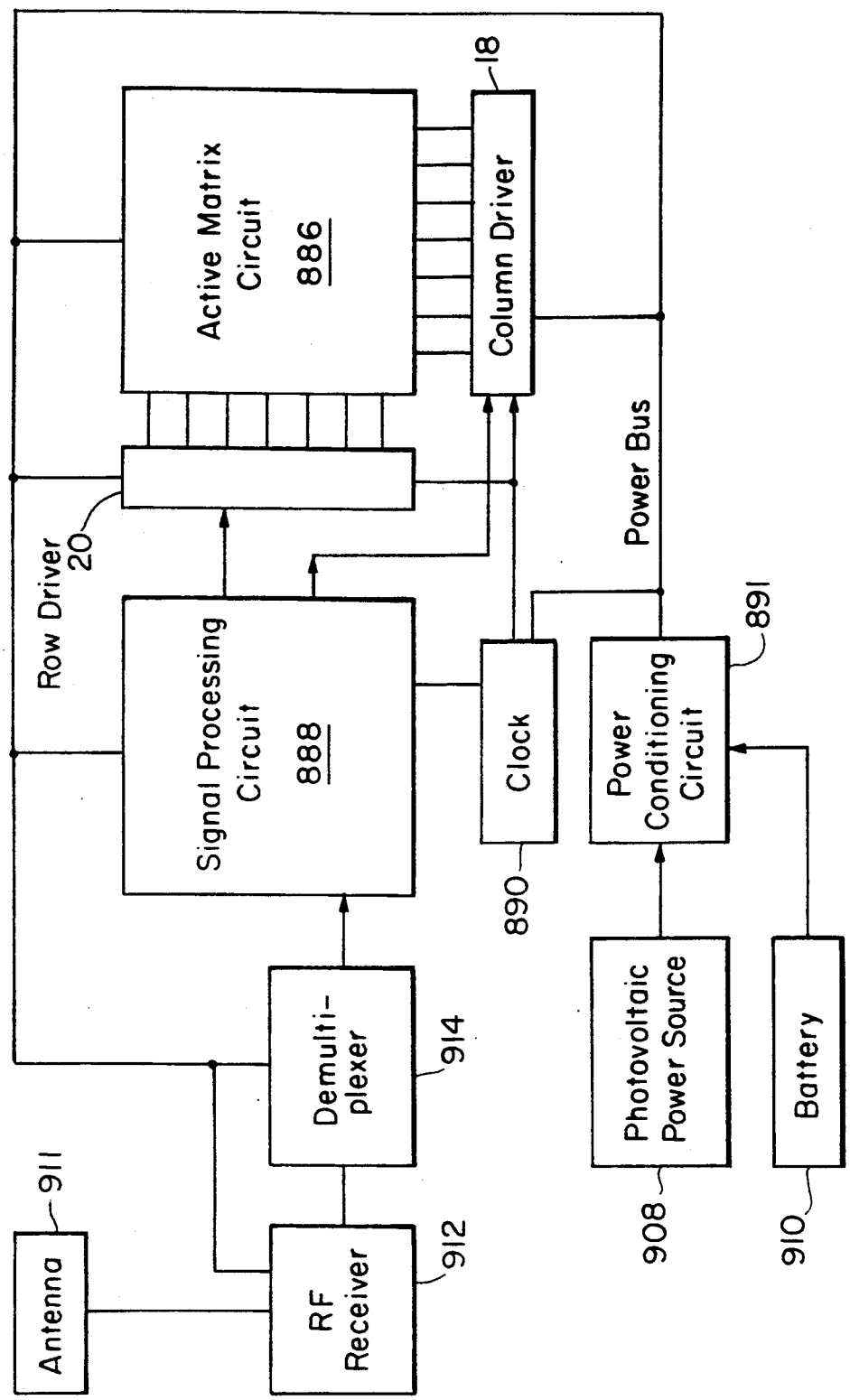
FIG. 34A-34B are circuit diagrams illustrating two preferred driver systems for the active matrix slide assembly of FIG. 33.
Figure 34B:
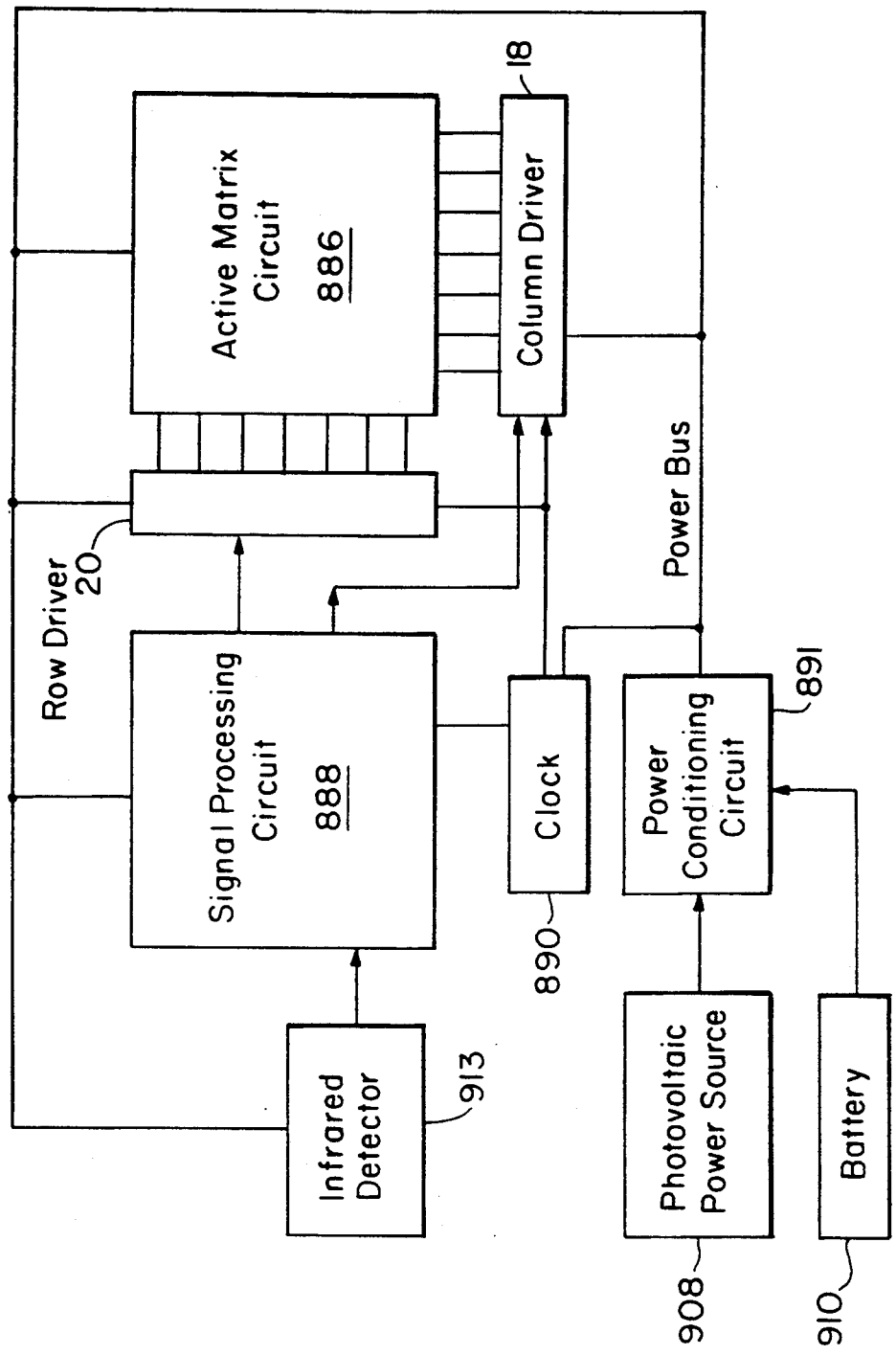

Driver circuitry for the active matrix slide assembly of FIG. 33 is illustrated in FIGS. 34A-34B. Referring to FIG. 34A, the driver circuitry includes the signal processing circuit 888, the system clock 890, the power conditioning circuit 891, column drivers 18, row drivers 20, a photovoltaic power source 908, a battery 910, an RF receiver 912 and an demultiplexer 914. The RF receiver 912 receives a stream of RF signals from the antenna 911. A demultiplexer 914 formats the RF signal stream such that it is can be processed by the previously-described signal processing circuit 888. The battery 910 and the photovoltaic power source 908, either individually or together, provide power to support the operations of the active matrix slide circuitry. The photovoltaic power source 908 can use slide projector light source energy to provide power to the active matrix slide and is therefore mounted onto the slide outer surface facing the light source (shown in FIG. 33).

Referring to FIG. 34B, the driver circuitry includes the signal processing circuit 888, the system clock 890, the power conditioning circuit 891, column drivers 18, row drivers 20, a photovoltaic power source 908, a battery 910 and an infrared detector photodiode 913. The photodiode 913 receives infrared signals from the electronics (not shown) which are processed by the signal processing circuit 888.

Figure 35:
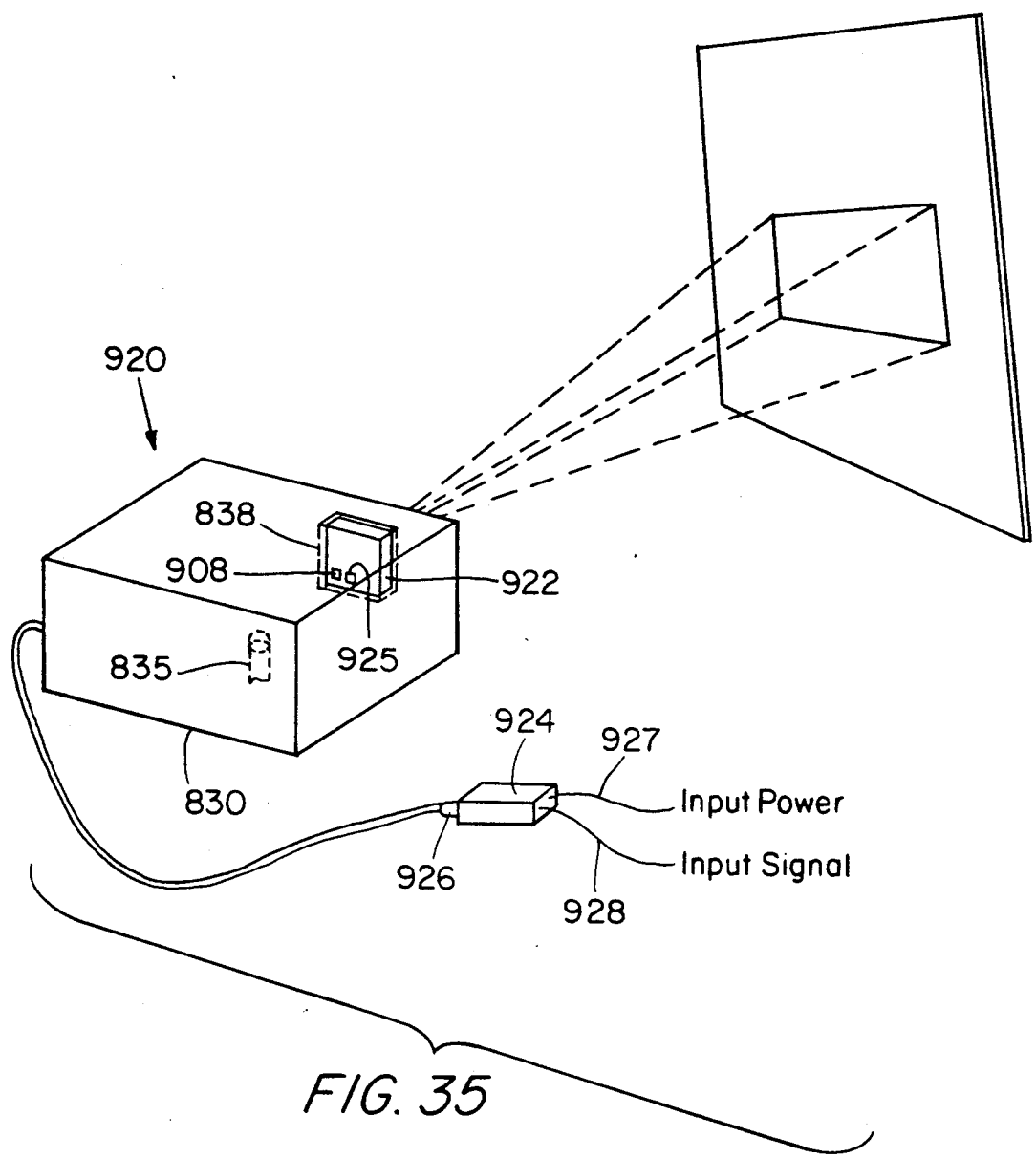
FIG. 35 is a perspective view of yet another embodiment of an active matrix slide assembly.

In another preferred embodiment shown in FIG. 35, an active matrix slide assembly 920 includes an AM slide 922 and an adapter unit 924. The slide 922 is dimensioned to be securely positioned in the chamber 838 for receiving light generated by the light source 835. A photovoltaic power source 908 is located on the slide 838 facing the light source 835 to provide power to the active matrix. The slide projector includes a plug 926 which is typically plugged into an electrical outlet (not shown) to receive electrical energy to power the projector light source 835. However, in this embodiment, the plug 926 is plugged into the adapter unit 924 to receive electrical energy. The adapter unit receives electrical energy via the input power line 927 and image information via the input signal line 928. The adapter unit, houses supporting electronics which couples encoded signals representing the received image information into incoming electrical energy received on line 927. The electrical energy with encoded image signals is directed to the plug 926 for providing power to the projector. The light source 835 converts some of the received electrical energy into light which is directed to the active matrix slide. As such, the encoded image signals are transmitted to the slide by the light source. A detector 925 is positioned on the slide for receiving the encoded signals.

Figure 36:
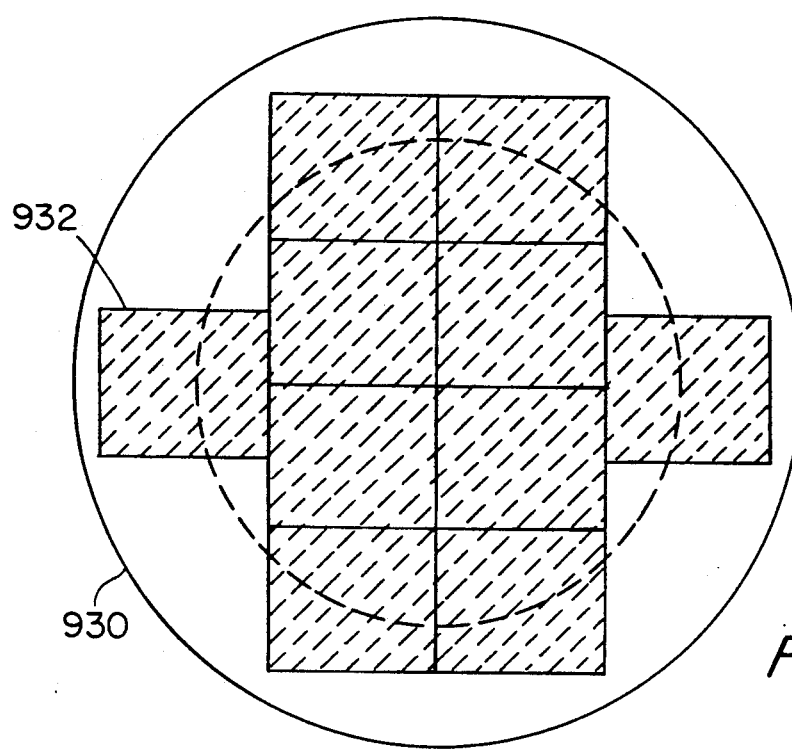
FIG. 36 is a top view of a semiconductor wafer which can be processed to provide a plurality of active matrices for use in active matrix slide assemblies.

As noted previously, an active matrix slide can be fabricated which has equivalent dimensions as a standard 35 mm slide. This can be accomplished because the previously described fabrication processes can produce a plurality of small active matrix circuit panels from a single wafer as shown in FIG. 36. Using a 6" silicon wafer 930, a number of active matrices can be produced from the wafer using any of the aforementioned processing techniques.

EQUIVALENTS

While this invention has been particularly shown and described with reference to preferred embodiments thereof, it will be understood by those skilled in the art that various changes in form and details may be made therein without departing from the spirit and scope of the invention as defined by the appended claims.

We claim:

1. A slide assembly for a display adapted for use with a slide projector having a projector body, a light source, an optical system and a chamber in which an image forming element can be placed for projection onto an external viewing surface, the slide assembly comprising:
   a housing adapted to be positioned over a slide projector body;
   an active matrix display slide movably mounted to the housing and having a storage position within the housing and an operating position outside of the housing, the display slide being movable from the storage position into the operating position such that the display slide can be positioned in a slide projector chamber when the display slide is in the operating position for selectively transmitting light from the light source to the optical system for projection of an image formed on the active matrix display slide onto the external viewing surface.

2. The slide assembly of claim 1 wherein the housing comprises an electronics unit for actuating the display slide, the actuated display slide selectively transmitting light to provide images.

3. The slide assembly of claim 2 wherein the electronics unit is adapted to receive computer data, the electronics unit responsive to the computer data actuating the display slide, the actuated display slide selectively transmitting light to provide computer-based images.

4. The slide assembly of claim 2 wherein the electronics unit is adapted to receive video signals, the electronics unit responsive to the video signal actuating the display slide, the actuated display slide selectively transmitting received light to produce video-based images.

5. The slide assembly of claim 1 wherein the display slide is adapted to produce multi-color images.

6. The slide assembly of claim 1 wherein the display slide comprises a light valve matrix secured between a pair of optically transmissive layers.

7. The slide assembly of claim 6 wherein the light valve matrix is secured to at least one of said optically transmissive layers with an adhesive.

8. The slide assembly of claim 1 wherein the display slide comprises a light valve matrix which comprises an array of transistors being formed in a semiconductor material, an array of electrodes with each electrode being electrically connected to at least one transistor and a light transmitting material through which received light from the light source is selectively transmitted.

9. The slide assembly of claim 8 wherein the light transmitting material comprises liquid crystal.

10. The slide assembly of claim 8 wherein the semiconductor material comprises single crystal silicon.

11. The slide assembly of claim 8 wherein each light valve comprises at least one transistor, an electrode and the light transmitting material.

12. The slide assembly of claim 8 wherein the display slide further comprises a driver circuit electrically connected to the light valve matrix for actuating the light valves.

13. The slide assembly of claim 1 further comprising an elongated arm having a proximal end coupled to the housing at a pivot point and a distal end coupled to the display slide such that the display slide is moved from the storage position into the operating position by a rotation of the arm about the pivot point.

14. The slide assembly of claim 1 wherein the display slide is linearly moved from the storage position into the operating position.

15. A slide assembly for light display adapted for use with a slide projector having a projector body, a light source, an optical system and a chamber in which an image forming element can be placed for projection onto an external viewing surface, the slide assembly comprising:
   a housing adapted to be positioned on a slide projector body;
   an electronics unit positioned within the housing; and
   an active matrix display slide electrically connected to an actuated by the electronics unit, the display slide moveable from a storage position within the housing to an operational position outside of the housing and being adapted to be positioned in a slide projector chamber when in the operational position for selectively transmitting light from the light source to provide images to the optical system for projection onto the external viewing surface.

16. The slide assembly of claim 15 further comprising an elongated arm having a proximal end coupled to the housing at a pivot point and a distal end coupled to the display slide such that the display slide is moved from the storage position into the operating position by a rotation of the arm about the pivot point.

17. The slide assembly of claim 15 wherein the display slide is linearly moved from the storage position into the operating position.

18. The slide assembly of claim 15 wherein the electronics unit is adapted to receive computer data, the electronics unit responsive to the computer data actuating the display slide, the actuated display slide selectively transmitting light to provide computer-based images.

19. The slide assembly of claim 15 wherein the electronics unit is adapted to receive video signals, the electronics unit responsive to the video signals actuating the display slide, the actuated display slide selectively transmitting received light to provide video-based images.

20. The slide assembly of claim 15 wherein the display slide is adapted to provide multi-color images.

21. The slide assembly of claim 15 wherein the display slide comprises a light valve matrix which comprises an array of transistors being formed in a semiconductor material, an array of electrodes with each electrode being electrically connected to at least one transistor and a light transmitting material through which received light from the light source is selectively transmitted.

22. The slide assembly of claim 21 wherein the light transmitting material comprises liquid crystal.

23. The slide assembly of claim 21 wherein the display slide further comprises a driver circuit electrically connected to the light valve matrix for actuating the light valves.

24. The slide assembly of claim 23 wherein the semiconductor material comprises a thin film of single crystal silicon material.

25. A light valve assembly for a display adapted for use in a slide projector, the assembly comprising:
an electronics unit within a housing adapted to be positioned over a slide projector;
a light valve module comprising a light valve array, each light valve of the light valve array including a transistor, an electrode and a material through which light can be selectively transmitted, each light valve being actuatable by a transistor, the light valve array being electrically connected to and controlled by the electronics unit, the module being moveable from a protected storage position within the housing to an exposed operational position outside of the housing adapted to be inserted into the slide projector such that the light valve array selectively transmits light via actuated light valves to provide projected images.

26. The light valve assembly of claim 25 wherein the array of transistors are formed in or on a semiconductor material.

27. The light valve assembly of claim 26 further comprising a driver circuit formed in or on the semiconductor material and connected to the electronics unit such that each transistor is electrically connected to and selectively driven by the driver circuit.

28. The light valve assembly of claim 26 wherein the semiconductor material comprises a thin film of single crystal silicon.

* * * * *